(12) United States Patent
Bonutti

(10) Patent No.: US 10,806,590 B2
(45) Date of Patent: *Oct. 20, 2020

(54) METHODS AND SYSTEMS FOR PROVIDING GENDER SPECIFIC PHARMACEUTICALS

(71) Applicant: P Tech, LLC, Manalapan, FL (US)

(72) Inventor: Peter M. Bonutti, Manalapan, FL (US)

(73) Assignee: P TECH, LLC, Manalapan, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/376,626

(22) Filed: Apr. 5, 2019

(65) Prior Publication Data

US 2019/0231542 A1    Aug. 1, 2019

Related U.S. Application Data

(60) Continuation of application No. 15/597,631, filed on May 17, 2017, which is a division of application No.
(Continued)

(51) Int. Cl.
*A61F 2/38* (2006.01)
*A61B 90/92* (2016.01)
(Continued)

(52) U.S. Cl.
CPC .............. *A61F 2/389* (2013.01); *A61B 34/10* (2016.02); *A61B 90/92* (2016.02); *A61B 90/94* (2016.02);
(Continued)

(58) Field of Classification Search
CPC ......... A61B 90/92; A61B 90/94; A61B 90/96; A61B 90/90; A61J 1/00; A61J 1/03
(Continued)

(56) References Cited

U.S. PATENT DOCUMENTS 3,627,122 A * 12/1971 Garbe, Jr. .............. A47B 87/02
116/308
3,837,478 A * 9/1974 Cunningham ......... B65D 41/62
206/427
(Continued)

FOREIGN PATENT DOCUMENTS

AU    2006325787    10/2013
CN    101330883    3/2013
(Continued)

OTHER PUBLICATIONS

Story, Mary; "Guidelines for Adolescent Nutrition Services"; 2005 (Year: 2005).*
(Continued)

*Primary Examiner* — Steven A. Reynolds
*Assistant Examiner* — Javier A Pagan
(74) *Attorney, Agent, or Firm* — Pillsbury Winthrop Shaw Pittman LLP

(57) ABSTRACT

The present disclosure provides a system of gender specific pharmaceuticals. The system includes a first package of a pharmaceutical for use by a male and a second package of a pharmaceutical for use by a female. The first package includes a pharmaceutical for use by a male and a first label coupled to the first package, wherein at least one of the first package and first label includes a male specifier and a recommended male dosage. The second package includes a pharmaceutical for use by a female and a second label coupled to the second package, wherein at least one of the second package and second label includes a female specifier and a recommended female dosage.

9 Claims, 14 Drawing Sheets

Related U.S. Application Data

15/003,243, filed on Jan. 21, 2016, now abandoned, which is a continuation of application No. 11/454,109, filed on Jun. 15, 2006, now Pat. No. 9,301,845.

(60) Provisional application No. 60/755,804, filed on Jan. 3, 2006, provisional application No. 60/690,653, filed on Jun. 15, 2005.

(51) Int. Cl.

| | | |
|---|---|---|
| *A61B 90/94* | (2016.01) | |
| *A61F 2/00* | (2006.01) | |
| *A61F 2/46* | (2006.01) | |
| *A61F 2/82* | (2013.01) | |
| *A61J 1/03* | (2006.01) | |
| *A61J 1/18* | (2006.01) | |
| *A61B 34/10* | (2016.01) | |
| *A61J 1/00* | (2006.01) | |
| *A61B 17/06* | (2006.01) | |
| *A61B 17/80* | (2006.01) | |
| *A61B 17/86* | (2006.01) | |
| *A61F 2/30* | (2006.01) | |
| *A61F 2/32* | (2006.01) | |
| *A61F 2/40* | (2006.01) | |
| *A61F 2/42* | (2006.01) | |
| *A61F 2/44* | (2006.01) | |
| *A61F 2/28* | (2006.01) | |
| *A61F 2/48* | (2006.01) | |

(52) U.S. Cl.
CPC .......... *A61F 2/0077* (2013.01); *A61F 2/0095* (2013.01); *A61F 2/38* (2013.01); *A61F 2/3859* (2013.01); *A61F 2/3877* (2013.01); *A61F 2/4657* (2013.01); *A61F 2/82* (2013.01); *A61J 1/00* (2013.01); *A61J 1/03* (2013.01); *A61J 1/18* (2013.01); *A61B 17/06166* (2013.01); *A61B 17/80* (2013.01); *A61B 17/86* (2013.01); *A61B 2034/108* (2016.02); *A61F 2/30767* (2013.01); *A61F 2/32* (2013.01); *A61F 2/3804* (2013.01); *A61F 2/40* (2013.01); *A61F 2/4202* (2013.01); *A61F 2/4261* (2013.01); *A61F 2/44* (2013.01); *A61F 2/461* (2013.01); *A61F 2002/2817* (2013.01); *A61F 2002/305* (2013.01); *A61F 2002/308* (2013.01); *A61F 2002/30032* (2013.01); *A61F 2002/30036* (2013.01); *A61F 2002/30064* (2013.01); *A61F 2002/3071* (2013.01); *A61F 2002/30092* (2013.01); *A61F 2002/3093* (2013.01); *A61F 2002/30112* (2013.01); *A61F 2002/30125* (2013.01); *A61F 2002/30153* (2013.01); *A61F 2002/30364* (2013.01); *A61F 2002/30383* (2013.01); *A61F 2002/30403* (2013.01); *A61F 2002/30563* (2013.01); *A61F 2002/30604* (2013.01); *A61F 2002/30616* (2013.01); *A61F 2002/30677* (2013.01); *A61F 2002/30878* (2013.01); *A61F 2002/30892* (2013.01); *A61F 2002/30909* (2013.01); *A61F 2002/30929* (2013.01); *A61F 2002/30975* (2013.01); *A61F 2002/3863* (2013.01); *A61F 2002/4631* (2013.01); *A61F 2002/4632* (2013.01); *A61F 2002/4633* (2013.01); *A61F 2002/4658* (2013.01); *A61F 2002/48* (2013.01); *A61F 2210/0019* (2013.01); *A61F 2220/0025* (2013.01); *A61F 2220/0033* (2013.01); *A61F 2230/0004* (2013.01); *A61F 2230/0008* (2013.01); *A61F 2230/0019* (2013.01); *A61F 2240/002* (2013.01); *A61F 2250/003* (2013.01); *A61F 2250/0031* (2013.01); *A61F 2250/0035* (2013.01); *A61F 2250/0067* (2013.01); *A61F 2250/0078* (2013.01); *A61F 2250/0085* (2013.01); *A61F 2250/0087* (2013.01); *A61F 2250/0089* (2013.01); *A61F 2310/0097* (2013.01); *A61F 2310/00544* (2013.01); *A61F 2310/00796* (2013.01); *A61J 2205/20* (2013.01); *A61J 2205/30* (2013.01); *A61J 2205/50* (2013.01); *A61J 2205/60* (2013.01)

(58) Field of Classification Search
USPC .................................................. 206/528, 534
See application file for complete search history.

(56) References Cited

U.S. PATENT DOCUMENTS

| | | | |
|---|---|---|---|
| 4,081,866 A | 4/1978 | Upshaw | |
| 4,340,978 A | 7/1982 | Buechel | |
| 4,457,307 A | 7/1984 | Stillwell | |
| 4,662,889 A | 5/1987 | Zichner | |
| 4,750,619 A | 6/1988 | Cohen | |
| 4,822,365 A | 4/1989 | Walker | |
| 4,883,180 A * | 11/1989 | Humphrey | A61J 7/04 206/534 |
| 4,888,020 A | 12/1989 | Horber | |
| 4,944,756 A | 7/1990 | Kenna | |
| 4,976,351 A * | 12/1990 | Mangini | G09F 3/0288 206/232 |
| 5,061,271 A | 10/1991 | Van Zile | |
| 5,133,758 A | 7/1992 | Hollister | |
| 5,137,536 A | 8/1992 | Koshino | |
| 5,148,920 A | 9/1992 | Walker | |
| 5,226,915 A | 7/1993 | Bertin | |
| 5,282,861 A | 2/1994 | Kaplan | |
| 5,326,361 A | 7/1994 | Hollister | |
| 5,356,006 A * | 10/1994 | Alpern | B65D 5/302 206/363 |
| 5,405,005 A | 4/1995 | White | |
| 5,445,642 A | 8/1995 | McNulty | |
| 5,549,686 A | 8/1996 | Johnson | |
| 5,597,384 A * | 1/1997 | Walker | A61F 2/0095 206/459.5 |
| 5,609,643 A | 3/1997 | Colleran | |
| 5,639,279 A | 6/1997 | Burkinshaw | |
| 5,681,354 A | 10/1997 | Eckhoff | |
| 5,688,279 A | 11/1997 | McNulty | |
| 5,728,162 A | 3/1998 | Eckhoff | |
| 5,762,125 A | 6/1998 | Mastraria | |
| 5,776,201 A | 7/1998 | Colleran | |
| 5,824,105 A | 10/1998 | Ries | |
| 5,840,011 A | 11/1998 | Tandgrebe | |
| 5,871,546 A | 2/1999 | Colleran | |
| 5,935,173 A | 8/1999 | Roger | |
| 6,013,103 A | 1/2000 | Kaufman | |
| 6,039,764 A | 3/2000 | Pottenger | |
| 6,059,111 A * | 5/2000 | Davila | B65D 5/5028 206/438 |
| 6,152,960 A | 11/2000 | Pappas | |
| 6,197,064 B1 | 3/2001 | Haines | |
| 6,233,524 B1 | 5/2001 | Harrell | |
| 6,258,126 B1 | 7/2001 | Colleran | |
| 6,264,697 B1 | 7/2001 | Walker | |
| 6,318,555 B1 * | 11/2001 | Kuske | A61F 13/5511 206/459.5 |
| 6,459,948 B1 | 10/2002 | Ateshian | |
| 6,471,060 B1 * | 10/2002 | Leyshon | A63H 3/50 206/472 |
| 6,540,786 B2 | 4/2003 | Chibrac | |
| 6,540,787 B2 | 4/2003 | Biegun | |
| 6,571,790 B1 * | 6/2003 | Weinstein | A61F 17/00 128/200.14 |
| 6,589,283 B1 | 7/2003 | Metzger | |

(56) References Cited

U.S. PATENT DOCUMENTS

| | | |
|---|---|---|
| 6,616,696 B1 | 9/2003 | Merchant |
| 6,699,291 B1 | 3/2004 | Augoyard |
| 6,712,856 B1 | 3/2004 | Carignan |
| 6,802,865 B2 | 10/2004 | Biegun |
| 6,827,723 B2 | 12/2004 | Carson |
| 6,893,467 B1 | 5/2005 | Bercovy |
| 6,901,304 B2 * | 5/2005 | Swan ............. G06Q 10/08 700/115 |
| 6,988,009 B2 | 1/2006 | Grimm |
| 7,081,137 B1 | 7/2006 | Servidio |
| 7,306,609 B2 | 12/2007 | Schmotzer |
| 7,309,360 B2 | 12/2007 | Tornier |
| 7,413,577 B1 | 8/2008 | Servidio |
| 7,468,075 B2 | 12/2008 | Lang |
| 7,534,263 B2 | 5/2009 | Burdulis |
| 7,618,451 B2 | 11/2009 | Berez |
| 7,634,119 B2 | 12/2009 | Tsougarakis |
| 7,717,956 B2 | 5/2010 | Lang |
| 7,796,791 B2 | 9/2010 | Tsougarakis |
| 7,799,077 B2 | 9/2010 | Lang |
| 8,062,377 B2 | 11/2011 | Haines |
| 8,088,167 B2 | 1/2012 | Haines |
| 8,545,569 B2 | 10/2013 | Fitz |
| 8,551,179 B2 | 10/2013 | Jones |
| 8,882,847 B2 | 11/2014 | Burdulis |
| 8,932,363 B2 | 1/2015 | Tsougarakis |
| 9,750,612 B2 * | 9/2017 | Bonutti ............. A61F 2/0077 |
| 2001/0045300 A1 | 11/2001 | Fincher |
| 2003/0055502 A1 | 3/2003 | Lang |
| 2003/0158606 A1 | 8/2003 | Coon |
| 2003/0196929 A1 * | 10/2003 | Gopinathan ......... A61J 1/00 206/570 |
| 2003/0216669 A1 | 11/2003 | Lang |
| 2003/0225458 A1 | 12/2003 | Donkers |
| 2004/0031722 A1 * | 2/2004 | Reed ............. B42D 15/045 206/575 |
| 2004/0031798 A1 * | 2/2004 | Fox ............. B29C 45/16 220/359.1 |
| 2004/0039450 A1 | 2/2004 | Griner |
| 2004/0045863 A1 * | 3/2004 | Rhoades ......... B65D 25/02 206/534 |
| 2004/0133276 A1 | 7/2004 | Lang |
| 2004/0138754 A1 | 7/2004 | Lang |
| 2004/0147927 A1 | 7/2004 | Tsougarakis |
| 2004/0172137 A1 | 9/2004 | Blaylock |
| 2004/0204644 A1 | 10/2004 | Tsougarakis |
| 2004/0204760 A1 | 10/2004 | Fitz |
| 2004/0208832 A1 * | 10/2004 | Bates ............. A61J 3/071 424/46 |
| 2004/0236424 A1 | 11/2004 | Berez |
| 2004/0249467 A1 | 12/2004 | Meyers |
| 2005/0029156 A1 * | 2/2005 | Girzaitis ............ A61J 7/04 206/570 |
| 2005/0102032 A1 | 5/2005 | Beynnon |
| 2005/0107884 A1 | 5/2005 | Johnson |
| 2005/0177169 A1 | 8/2005 | Fisher |
| 2005/0183982 A1 * | 8/2005 | Giewercer ........ A61J 7/04 206/534 |
| 2005/0234461 A1 | 10/2005 | Burdulis |
| 2005/0240441 A1 * | 10/2005 | Suzuki ........... G06Q 10/10 705/2 |
| 2005/0267584 A1 | 12/2005 | Burdulis |
| 2005/0283249 A1 | 12/2005 | Carson |
| 2005/0283250 A1 | 12/2005 | Coon |
| 2005/0283251 A1 | 12/2005 | Coon |
| 2005/0283252 A1 | 12/2005 | Coon |
| 2005/0283253 A1 | 12/2005 | Coon |
| 2006/0042990 A1 * | 3/2006 | Galuten .......... A61F 13/02 206/570 |
| 2006/0111722 A1 | 5/2006 | Bouadi |
| 2006/0129246 A1 | 6/2006 | Steffensmeier |
| 2006/0224244 A1 | 10/2006 | Thomas |
| 2006/0235541 A1 | 10/2006 | Hodorek |
| 2006/0235542 A1 | 10/2006 | Hodorek |
| 2007/0028491 A1 * | 2/2007 | Panella ............ G09F 3/00 40/324 |
| 2007/0088444 A1 | 4/2007 | Hodorek |
| 2007/0123984 A1 | 5/2007 | Hodorek |
| 2007/0135926 A1 | 6/2007 | Walker |
| 2007/0179607 A1 | 8/2007 | Hodorek |
| 2007/0233269 A1 | 10/2007 | Steines |
| 2007/0250169 A1 | 10/2007 | Lang |
| 2007/0260323 A1 | 11/2007 | Earl |
| 2008/0000786 A1 * | 1/2008 | Collotta ............ B65D 51/28 206/217 |
| 2008/0058947 A1 | 3/2008 | Earl |
| 2008/0058948 A1 | 3/2008 | Biegun |
| 2008/0097616 A1 | 4/2008 | Meyers |
| 2008/0119940 A1 | 5/2008 | Otto |
| 2008/0140212 A1 | 6/2008 | Metzger |
| 2008/0188855 A1 | 8/2008 | Brown |
| 2008/0188937 A1 | 8/2008 | Ribic |
| 2008/0188942 A1 | 8/2008 | Brown |
| 2008/0243258 A1 | 10/2008 | Sancheti |
| 2008/0281428 A1 | 11/2008 | Meyers |
| 2008/0288080 A1 | 11/2008 | Sancheti |
| 2009/0036992 A1 | 2/2009 | Tsakonas |
| 2009/0043339 A1 | 2/2009 | Hotokebuchi |
| 2009/0062924 A1 | 3/2009 | Kito |
| 2009/0105772 A1 | 4/2009 | Seebeck |
| 2009/0222103 A1 | 9/2009 | Fitz |
| 2009/0255843 A1 * | 10/2009 | Krakowski ......... A61M 35/00 206/534 |
| 2009/0265011 A1 | 10/2009 | Mandell |
| 2009/0265013 A1 | 10/2009 | Mandell |
| 2009/0306786 A1 | 12/2009 | Samuelson |
| 2009/0306787 A1 | 12/2009 | Crabtree |
| 2009/0319047 A1 | 12/2009 | Walker |
| 2009/0319048 A1 | 12/2009 | Shah |
| 2009/0319049 A1 | 12/2009 | Shah |
| 2009/0326663 A1 | 12/2009 | Dun |
| 2009/0326665 A1 | 12/2009 | Wyss |
| 2009/0326666 A1 | 12/2009 | Wyss |
| 2009/0326667 A1 | 12/2009 | Williams |
| 2010/0036499 A1 | 2/2010 | Pinskerova |
| 2010/0036500 A1 | 2/2010 | Heldreth |
| 2010/0042224 A1 | 2/2010 | Otto |
| 2010/0161067 A1 | 6/2010 | Saleh |
| 2010/0191298 A1 | 7/2010 | Earl |
| 2010/0305708 A1 | 12/2010 | Lang |
| 2010/0329530 A1 | 12/2010 | Lang |
| 2011/0022179 A1 | 1/2011 | Andriacchi |
| 2011/0093083 A1 | 4/2011 | Earl |
| 2011/0123506 A1 * | 5/2011 | Hickle ............ A23L 33/30 424/94.1 |
| 2011/0144760 A1 | 6/2011 | Wong |
| 2011/0218541 A1 | 9/2011 | Bailey |
| 2011/0307067 A1 | 12/2011 | Dees |
| 2012/0323334 A1 | 12/2012 | Jones |
| 2012/0323335 A1 | 12/2012 | Parisi |
| 2012/0323336 A1 | 12/2012 | Parisi |
| 2012/0323337 A1 | 12/2012 | Parisi |
| 2013/0006370 A1 | 1/2013 | Wogoman |
| 2013/0006371 A1 | 1/2013 | Wogoman |
| 2013/0006376 A1 | 1/2013 | Wogoman |
| 2013/0006378 A1 | 1/2013 | Wogoman |
| 2013/0226305 A1 | 8/2013 | Donno |

FOREIGN PATENT DOCUMENTS

| | | |
|---|---|---|
| CN | 103732186 | 4/2014 |
| DE | 202007014126 | 1/2008 |
| EP | 0303467 | 2/1989 |
| EP | 0376658 | 6/1994 |
| EP | 0381352 | 6/1994 |
| EP | 0567705 | 7/1997 |
| EP | 0993812 | 4/2000 |
| EP | 1013232 | 6/2000 |
| EP | 1285638 | 2/2003 |
| EP | 1033117 | 6/2004 |
| EP | 0975286 | 8/2004 |
| EP | 1477142 | 11/2004 |

(56) References Cited

FOREIGN PATENT DOCUMENTS

| | | |
|---|---|---|
| EP | 1477143 | 11/2004 |
| EP | 1285638 | 11/2005 |
| EP | 1719478 | 11/2006 |
| EP | 1862150 | 12/2007 |
| EP | 2004099 | 12/2008 |
| EP | 1867302 | 9/2009 |
| EP | 2147660 | 1/2010 |
| EP | 2158878 | 3/2010 |
| EP | 1555962 | 2/2011 |
| EP | 2324799 | 5/2011 |
| EP | 2335654 | 6/2011 |
| FR | 2901996 | 12/2007 |
| JP | 3267055 | 11/1991 |
| JP | 0553501 | 3/1993 |
| JP | 0568987 | 3/1993 |
| JP | 149908 | 6/1997 |
| JP | 11504226 | 4/1999 |
| JP | 11511347 | 10/1999 |
| JP | 34369972 | 11/2003 |
| JP | 3495161 | 2/2004 |
| JP | 2004166802 | 6/2004 |
| JP | 2005532089 | 10/2005 |
| JP | 2009519781 | 5/2009 |
| JP | 4820547 | 11/2011 |
| WO | 1995035074 | 12/1995 |
| WO | 1996003939 | 2/1996 |
| WO | 200203010 | 4/2000 |
| WO | 2003094782 | 11/2003 |
| WO | 2004016204 | 2/2004 |
| WO | 2005037147 | 4/2005 |
| WO | 2005051240 | 6/2005 |
| WO | 2005129967 | 12/2005 |
| WO | 2006058057 | 6/2006 |
| WO | 2007054553 | 5/2007 |
| WO | 2007109641 | 9/2007 |
| WO | 2008054389 | 5/2008 |
| WO | 2009088234 | 7/2009 |
| WO | 2009088236 | 7/2009 |
| WO | 2009088238 | 7/2009 |
| WO | 2009105495 | 8/2009 |
| WO | 2010108550 | 9/2010 |
| WO | 2011072235 | 6/2011 |
| WO | 2012031774 | 3/2012 |
| WO | 2012112698 | 8/2012 |
| WO | 2012173704 | 12/2012 |
| WO | 2012173706 | 12/2012 |
| WO | 2012173740 | 12/2012 |

OTHER PUBLICATIONS

Non-Final Office Action dated Jun. 7, 2017 relating to U.S. Appl. No. 15/457,534, 19 pages.

Hitt et al., "Anthropometric Measurements of the Human Knee: Correlation to the Sizing of Current Knee Arthroplasty Systems," (J. of Bone & Joint Surg., 2003).

Article: Dimensions of the Knee—Radiographic and autopsy study of sizes required for a knee prosthesis, B.B. Seedhom et al., Annals of the Rheumatic Diseases (1972), pp. 54-58 (Seedhom).

Merriam-Webster.com—On-line Dictionary—definition "prosthesis" retrieved Apr. 26, 2010.

OrthoKnow® (pp. 1-4) editorial, Strategic Insights into the Orthopaedic Industry, Apr. 2006; © 1997-2006 Knowledge Enterprises, Inc.

Zimmer Gender Solutions Questions & Answers, © 2005 Zimmer, Inc.

Women and Men are Different, Confidence Shaping Successful Outcomes Using Gender Solutions High-Flex Femorals, Zimmer Gender Solutions, © 2006 Zimmer, Inc.

Non-Final Office Action dated Dec. 31, 2008 relating to U.S. Appl. No. 11/454,109, 6 pgs.

Final Office Action dated Aug. 12, 2009 relating to U.S. Appl. No. 11/454,109, 8 pgs.

Non-Final Office Action dated Jan. 26, 2010 relating to U.S. Appl. No. 11/454,109, 8 pgs.

Final Office Action dated Sep. 14, 2010 relating to U.S. Appl. No. 11/454,109, 9 pgs.

Final Office Action dated Aug. 3, 2012 relating to U.S. Appl. No. 11/454,109, 9 pgs.

Non-Final Office Action dated Jul. 11, 2014 relating to U.S. Appl. No. 11/454,109, 10 pgs.

Final Office Action dated Feb. 6, 2015 relating to U.S. Appl. No. 11/454,109, 11 pgs.

Non-Final Office Action dated Jul. 13, 2015 relating to U.S. Appl. No. 11/454,109, 13 pages.

Final Office Action dated Oct. 22, 2015 relating to U.S. Appl. No. 11/454,109, 11 pages.

Non-Final Office Action dated Jun. 29, 2016 relating to U.S. Appl. No. 15/003,243, 5 pgs.

* cited by examiner

METHODS AND SYSTEMS FOR PROVIDING GENDER SPECIFIC PHARMACEUTICALS

CROSS-REFERENCE TO RELATED APPLICATIONS

This application is a continuation of U.S. patent application Ser. No. 15/597,631 entitled Gender Specific Implant and Packaging, filed May 17, 2017, which is a division of U.S. patent application Ser. No. 15/003,243 entitled Gender Specific Implant and Packaging, filed Jan. 21, 2016, now abandoned, which is a continuation of U.S. patent application Ser. No. 11/454,109 entitled Implant for Knee Replacement, filed Jun. 15, 2006, now U.S. Pat. No. 9,301,845, which claims the benefit of U.S. Provisional Application No. 60/755,804 entitled Gender Specific Implant and Packaging, filed Jan. 3, 2006, and U.S. Provisional Application No. 60/690,653 entitled Gender Specific Implant and Packaging, filed Jun. 15, 2005, the contents of which are each herein incorporated by reference in their entirety.

FIELD OF THE INVENTION

The present invention relates to gender specific pharmaceuticals.

BACKGROUND OF THE INVENTION

Some fields of study recognize and account for differences between men and women better than others. Psychologists, for example, may choose different therapeutic techniques to address certain emotional issues with a man than with a woman. Personal trainers likewise may employ different physical training regimen for men than for women, and may have different target goals for cardiovascular and muscular development.

Some fields of medical study may even consider gender during diagnosis of an illness or injury, but most do not identify or consider gender differences in treatment protocols, medical implants, drug development, drug dosage and delivery, and the like. Instead, many treatments only account for differences based on body weight, or create distinctions only between infants, children and adults while ignoring potentially significant differences based on gender. In many instances, therefore, there has been little, if any, effort to refine medical science to account for differences between men and women.

One reason that medical science has not advanced to account for gender differences in treatment may be due in part to a widely held perception that sexual dimorphism is relatively low in humans when compared to other animals, and therefore the differences often are ignored or overlooked. Sexual dimorphism is the systematic difference in form between individuals of different gender in the same species. This may include differences in size, color, or the presence of gender defining body parts, such as horns or antlers. While in humans, the male and female forms are perceived differently, they tend to have a low level of sexual dimorphism when compared to other species. For example, the body masses of both male and female humans are approximately normally distributed.

However, despite this relative low-level sexual dimorphism when compared to other species, there are physiological, muscular, and skeletal differences in men and women that are of particular relevance to improved medical treatment. Many of these differences are present even between men and women of similar height, weight, and build, but currently are not taken into consideration when treating a patient. For example, the female brain has more intercellular connections than the male brain, which may account for why women generally are likely to recover more of their speech abilities after a stroke than men, yet medical treatment for men and women is virtually identical. Additionally, male bones tend to be larger in size, having greater lengths, thicknesses, and densities. Similarly, the joints in male and female bodies differ. For example, the notch width at the end of the femur in the knee joint tends to be wider in males than in females. Despite these differences, medical implants currently are limited to unisex designs. Further examples of differences between men and women may be found in metabolic rates, diurnal changes, range of motion, pH and hormonal changes, elasticity of body tissue, and susceptibility to diseases or medical conditions.

For example, males and females metabolize medications at different rates and react differently to different types of medications. As a result of these differences, females may metabolize some analgesics and adjuvant drugs at different rates than men, among them oxycodone, tramadol, fentanyl, bupivacaine, and diazepam. Similarly, males may respond more favorably to tricyclic agents and females may get greater relief from selective serotonin reuptake.

In spite of these differences, medical practitioners tend to treat male and female patients with a gender-neutral approach. At best, medicines may be prescribed based on weight or body mass index (BMI), without taking into account other, potentially more significant gender differences. Medical implants and instruments are provided in limited sizes (e.g., small, medium, and large), but each having similar geometric proportions, the same material construction, the same surface treatment, and the same therapeutic coating for men and women. In short, medical science has made little effort to account for many potentially significant gender differences.

Perhaps another reason gender differences have not been incorporated into medical science is the additional complexity it would introduce for patients and health professionals. It may be difficult, for example, for a doctor, nurse, or pharmacist to keep track of different gender-specific dosage amounts, dosage rates, drug combinations, and the like. Likewise, a couple, such as a husband and wife, where both are being treated for the same medical condition may become confused if presented with different medicines, or with different dosage instructions (e.g. dosage amounts, dosage frequency, etc.) for medicines with the same active ingredient. Additionally, if both patients are taking the same brand of medication, it may be difficult to distinguish each person's medicine from the other.

Regardless of the reason for the current state of medical science, it would be desirable to have more sophisticated medical treatments that better account for gender differences.

SUMMARY OF THE INVENTION

The present invention provides a system and method for accounting for gender specific differences in medical treatment. This is achieved first by taking into account these differences so that a patient's therapy and treatment is more closely tailored to them. This includes, for example, providing gender specific treatment, medical devices, medicines, and/or instrumentation. These differences may result in different techniques being provided for treating bones or joints (such as the knee, hip, or spine), differences in drug selection, drug delivery and dosage, different implant designs, and different treatment for soft tissue repair. These and other non-limiting examples are further discussed in detail below.

In addition, the invention also may involve improved identification systems that help patients or health professionals avoid or reduce potential confusion that may result from the availability of gender specific treatment options. For example, the medical treatment system can include a medical device identification system which differentiates use for male and female patients. The medical device identification system includes a container adapted to receive a medical device and a gender specifier. The gender specifier is used to identify the gender the medical device is designed for. The gender specifier can be incorporated into a label, where the gender specifier can be in text form, symbolic form or color coded. For example, the gender specifier can be in the text form "MALE" or "FEMALE."

The gender specifier may also be an electronic device, such as an RFID tag that is associated or packaged with the device or medicine so that it can be readily identified and associated for use with a particular gender. This embodiment of the invention may be of particular use for sterilized products, medicines that are sealed in a container, or in other situations where it is difficult to visually confirm for which sex the product is intended.

Alternatively, the medical treatment system may include a medication container having a gender-specific labeling system. The label system may provide information identifying the contents and gender-specific instructions regarding usage of the enclosed medicine. The usage information may include, for example, the recommended dosage for one or both genders. Thus, the gender specifier may be dosage information, but also it may be in a text form, such as "FEMALE" and "MALE," or alternatively may be in the form of a color coding or in symbolic representations.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention provides a system and method for gender specific medical treatment. As mentioned above, gender differences are often ignored when determining how to treat a medical condition. It is believed that accounting for one or more of these differences during treatment may greatly improve the quality of care and degree of recovery that a patient experiences.

One example where medical science currently applies a unisex approach is in the treatment of bones and joints. Three non-limiting examples discussed below—namely treatment of the knee, hip, and spine—illustrate how the invention may be used to improve the quality of care a patient may receive when gender differences are taken into account.

Knee replacements, for instance, are about twice as likely to be performed on women as on men. There are gender-specific differences in the bones and joint associated with the knee that are not currently taken into account in this area of medicine. For example, the female patella is generally thinner and narrower in superior and inferior dimensions, while in men it is generally wider in proportion.

Figure 1:
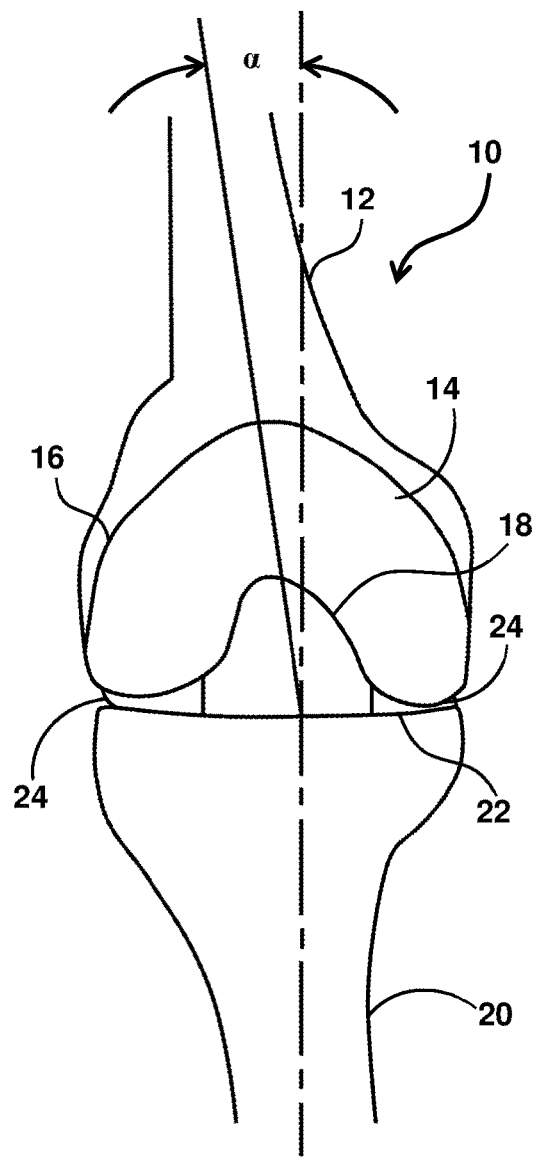
FIG. 1 depicts an exemplary knee joint.

Referring to FIG. 1, there is shown an anterior view of a knee joint 10, wherein the patella is not shown. The knee joint 10 includes a femoral portion 12 having medial and lateral condyles 14 and 16. A trochlear groove 18 is interposed between the medial and lateral condyles 14 and 16, allowing for tracking of the patella along the end portion of the femur 12 as the knee joint 10 is flexed and extended. A tibial portion 20 of the knee joint 10 includes a tibial plateau 22, including medial and lateral menisci 24 and 26 disposed on the tibial plateau 22. The medial and lateral condyles 14 and 16 abut the tibial plateau 22, engaging the medial and lateral menisci 24 and 26 allow for rotation of the tibia 20 with respect to the femur 12 and shock absorption between the femur 12 and tibia 20. A central longitudinal axis of the femur portion 12 is aligned at an angle a with respect to a central longitudinal axis of the tibial portion 20.

Figure 2:
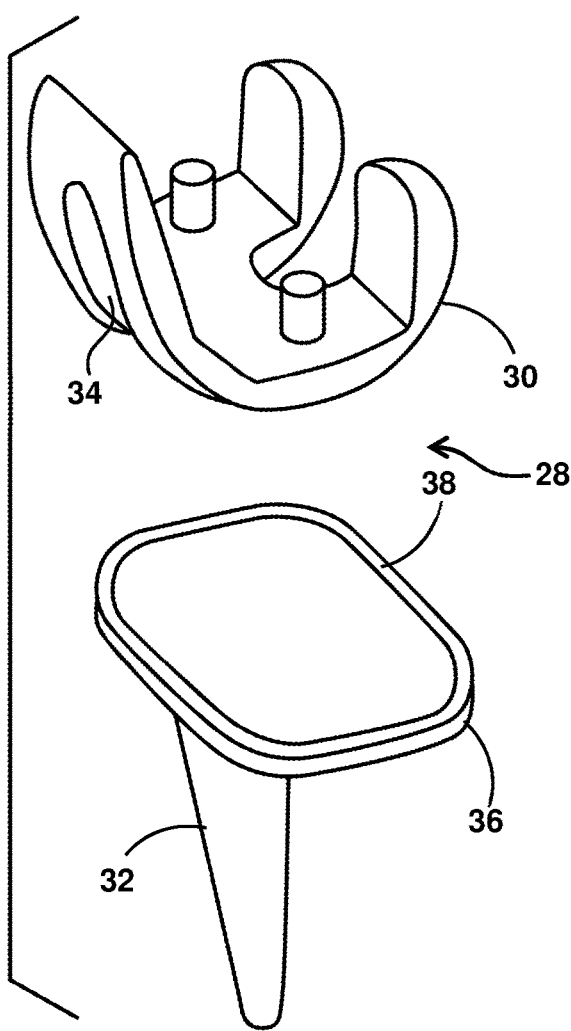
FIG. 2 depicts an exemplary prosthetic knee joint.

Depending upon the degree and type of injury, a total or partial knee replacement procedure can be performed when a knee joint 10 is damaged. A total knee replacement may involve replacing or repairing up to three bone surfaces, namely the medial and lateral condyles 14 and 16 of the femur 12, the tibial plateau 22 of the tibia 20, and the back surface of the patella. Referring to FIG. 2, an exemplary prosthetic knee 28 includes a femoral component 30 and a tibial component 32. The femoral component 30 is configured to curve about the cut end portions of the medial and lateral condyles 14 and 16, having a trochlear groove 34 therein to allow tracking of the patella about the femoral component 30 as the knee joint 10 is flexed and extended. The tibial component 32 includes flat platform 36 with a cushioning material 38, replacing the medial and lateral meniscus 24 and 26.

The femoral and tibial components 30 and 32 cooperate to permit normal knee-joint functioning. The femoral and tibial components 30 and 32 are designed similar in size and shape to average knee joints, and have a range of sizes to span the normal size ranges of the knee joints.

As previously discussed, there are many skeletal differences between men and women, including bone structure, configuration, size, length, thickness, density, and geometric proportion. The male femur, for example, tends to be proportionally wider, has a greater thickness, and a wider trochlear groove. Additionally, because of the differences between the male and female pelvic structures, the angular relationship a. between the femur and the tibia in male and female knees is different. Currently, these differences are not accounted for in prosthetic design, whereas in the present invention one or more of these differences could be taken into account to provide gender-specific prosthetic design.

Thus, one aspect of the present invention is directed to a prosthetic knee joint that is configured and dimensioned for gender specific use. To improve articulation for women, for instance, the prosthetic knee joint may have a reduced bearing surface, such as being reduced by 10 percent or more in comparison to a male prosthetic knee design. The reduced bearing surface would allow greater range of motion of the implant corresponding to the greater range of motion typically exhibited in women. Overall, the implant for women may also be significantly thinner, such as being at least 5 percent thinner, at least 10 percent thinner, or alternatively at least 20 percent thinner than implants for men. A formal prosthetic knee for women may also have one or more of the following: thinner runners to help improve range of motion, lesser amount of metal, or greater flexibility.

If the female implant is significantly thinner or has a much smaller surface area contacting bone than a male implant, it may be desirable to provide more ingrowth surface on the female implant in order to enhance fixation. Fixation can also be increased by using a different amount or configuration of bone cement, the grouting material frequently used for fixation of a prosthetic component. In this regard, the present invention also contemplates female specific and male specific bone cement, with the composition of the female bone cement differing from the male bone cement. For example, fillers could be added to the PMMA (the principal component of the bone cement) to change the mechanical properties. Additionally, other components (such as an antibiotic) can be selected depending on whether the intended recipient is a male or a female. In this regard, a female bone cement may have added components to address the osteoporotic bone found in women. Such components include calcium supplements and other agents for promoting an osteogenic or osteoconductive effect (or slowing the process of bone demineralization).

Figure 3:
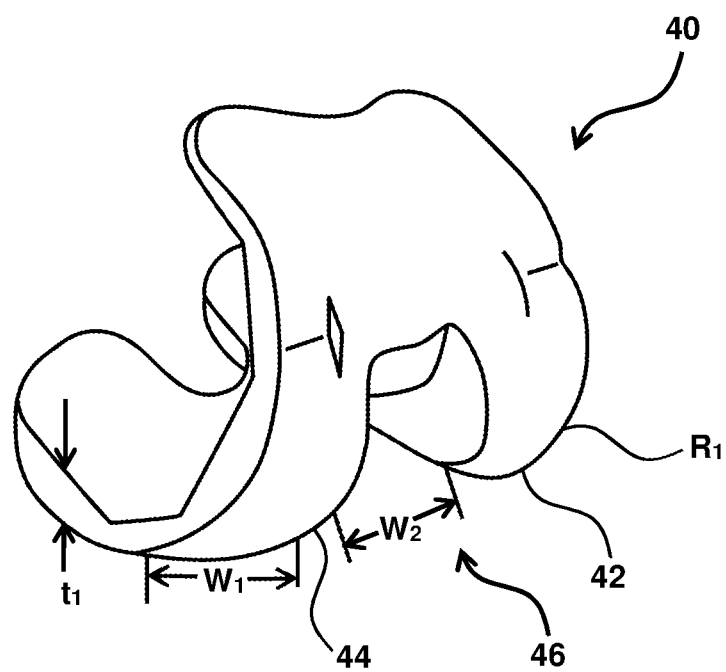
FIG. 3 depicts an exemplary femoral component of a male prosthetic knee joint.

Referring to FIG. 3, a male femoral component 40 of a knee joint implant of the present invention is provided. The femoral component 40 includes medial and lateral condyle portions 42 and 44 each having a width $W_1$ and a radius $R_1$. A trochlear groove 46 is disposed between the medial and lateral condyle portions 42 and 44 and has a width W2. The widths W1 and W2 and the radius R1 of the femoral components 40 are provided in a range of sizes to span the normal size ranges of male human knee joints. Additionally, the thickness $t_1$ and the material densities of the femoral components 40 are selected to correspond to male bone thickness and densities.

Figure 4:
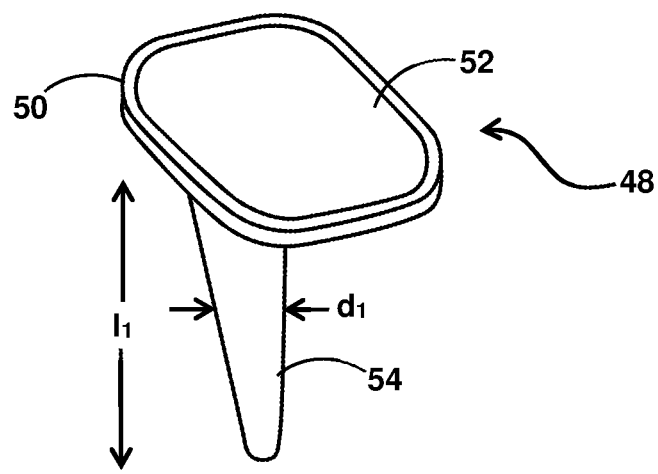
FIG. 4 depicts an exemplary tibial component of a male prosthetic knee joint.

Referring to FIG. 4, a male tibial component 48 of a knee joint of the present invention is provided. The tibial component 48 includes flat platform 50, having a substantially oval shape, wherein the cushioning material 52 replaces the medial and lateral meniscus 24 and 26. A bone spike 54 is included for insertion into the prepared end of the tibia, securing the tibial component 48 to the tibia. The bone spike 54 can be substantially conical in shape, having a maximum diameter $d_1$ and length $l_1$.

Figure 5:
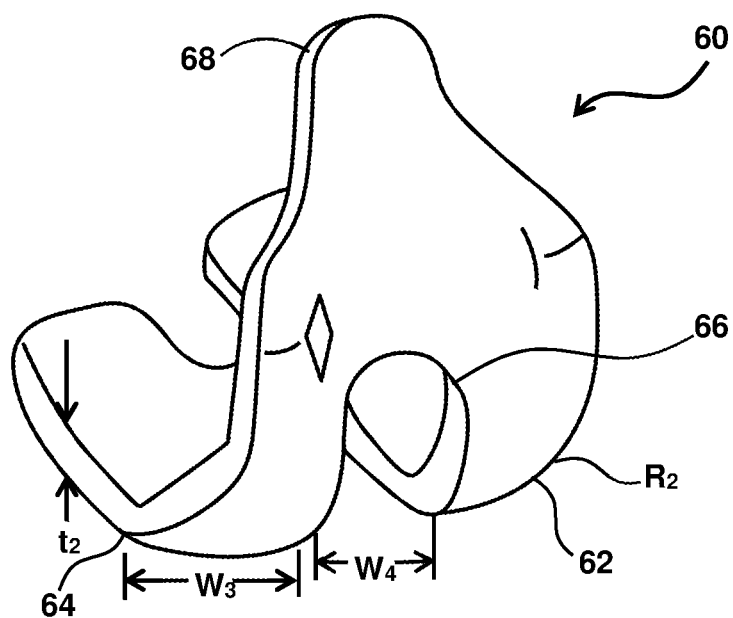
FIG. 5 depicts an exemplary femoral component of a female prosthetic knee joint.

Referring to FIG. 5, a female femoral component 60 of a knee joint implant of the present invention is provided. The femoral component 60 includes medial and lateral condyle portions 62 and 64 each having a width $W_3$ and a radius $R_2$. A trochlear groove 66 is disposed between the medial and lateral condyle portions 62 and 64 and has a width $W_4$. The widths $W_3$ and $W_4$ and the radius $R_2$ of the femoral components 60 are provided in a range of sizes to span the normal size ranges of female human knee joints. Additionally, the thickness $t_2$ and the material densities of the femoral components 60 are selected to correspond to female bone thickness and densities.

Figure 6:
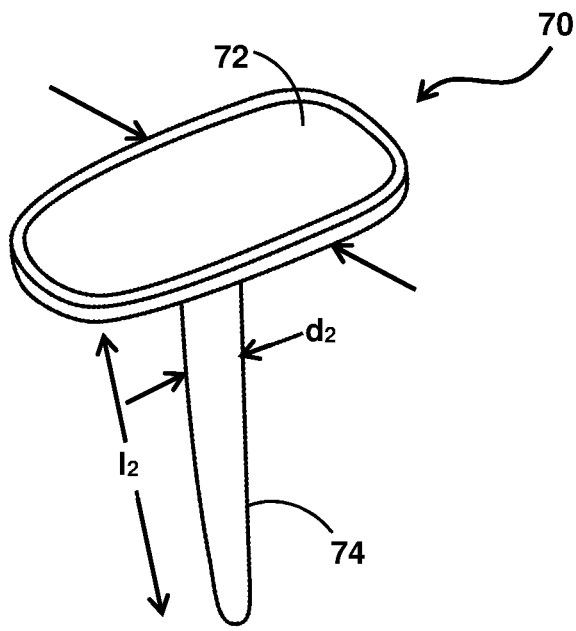
FIG. 6 depicts an exemplary tibial component of a female prosthetic knee joint.

Referring to FIG. 6, female tibial component 70 of a knee joint of the present invention is provided.

The tibial component 70 includes flat platform 72, having a substantially elongated oval shape, wherein the cushioning material 74 replaces the medial and lateral meniscus 24 and 26. A bone spike 76 is included for insertion into the prepared end of the tibia, securing the tibial component 70 to the tibia. The bone spike 74 can be substantially conical in shape, having a maximum diameter $d_2$ and length h.

As previously discussed, the male femoral component 40 will generally have greater widths $W_1$ and $W_2$ and the radius $R_1$, thus bearing surface area, than that of comparable female femoral component 60 widths $W_3$ and $W_4$ and the radius $R_2$. Similarly, the male femoral component 40 will generally have a greater material thickness $t_1$ than that of thickness $t_2$ of a comparable female femoral component 60. Thus, a "large" size for a male prosthetic knee joint may differ significantly in size, proportion, and construction from a large-sized prosthetic knee joint for women. Furthermore, as shown in FIG. 5, an upper section 68 of the female femoral component 60 can be generally narrower than that of a comparably male femoral component 40, to accommodate structural differences between the female and male femurs. In other words the female femoral component 60 design can have scalloped edges compared to the male femoral component 40 design. Additionally, the thickness, the material densities, and the material composition of the femoral components 40 and 60 may be selected to correspond to different male and female bone thickness and densities. Additional dimensions of the femoral portion of the knee joint can be utilized in the design and configuration of the femoral components 40 and 60.

Similar to the femoral components 40 and 60, the tibial components 58 and 70 are designed and configured for use in replacement of the knee joint in males and females. The dimensions of the tibial components once again may be provided in a range of sizes to span the normal size ranges of male and female human knee joints. As shown in FIGS. 4 and 6, the male platform 50 has a substantially oval shape, whereas the female platform 72 has an elongated oval shape. The shapes of the platforms 50 and 72 are selected to accommodate the differences in sizes and bearing surface areas of the corresponding male and female femoral components 48 and 60. Additionally, the thickness and the material densities of the tibial components are selected to correspond to or function with male and female bone thickness, densities, geometry, range of motion, or the like. Furthermore, additional dimensions of the tibial portion of the knee joint can be utilized in the design and configuration of the tibial components 48 and 70.

Thus, a gender-specific design may be identified by one component having less material than for the opposite sex. Furthermore, additional dimensions of the femoral portion of the knee joint can be utilized in the design and configuration of the femoral components. One or more of these dimensions may be varied so that an implant is more suited to a male or female patient. Thus, an implant design may be considered gender-specific if one or more of these parameters has been selected to better match either a male or female.

A gender-specific prosthetic design may also be identified by comparing relative differences that exist between a female design and a male design. For example, if one or more dimensions (e.g., bearing surface area, widths, radii, curvature, thickness of material, amount of metal, range of motion, flexibility, etc.) or relative proportions (e.g., relative width or relative differences in angles, minimum or maximum sizes, etc.) or an implant design for one sex varies by more than 5 percent, or alternatively by 10 percent or more, or even by about 20 percent or more, from an implant designed for the opposite sex, then the design may qualify as being gender-specific.

Figure 7:
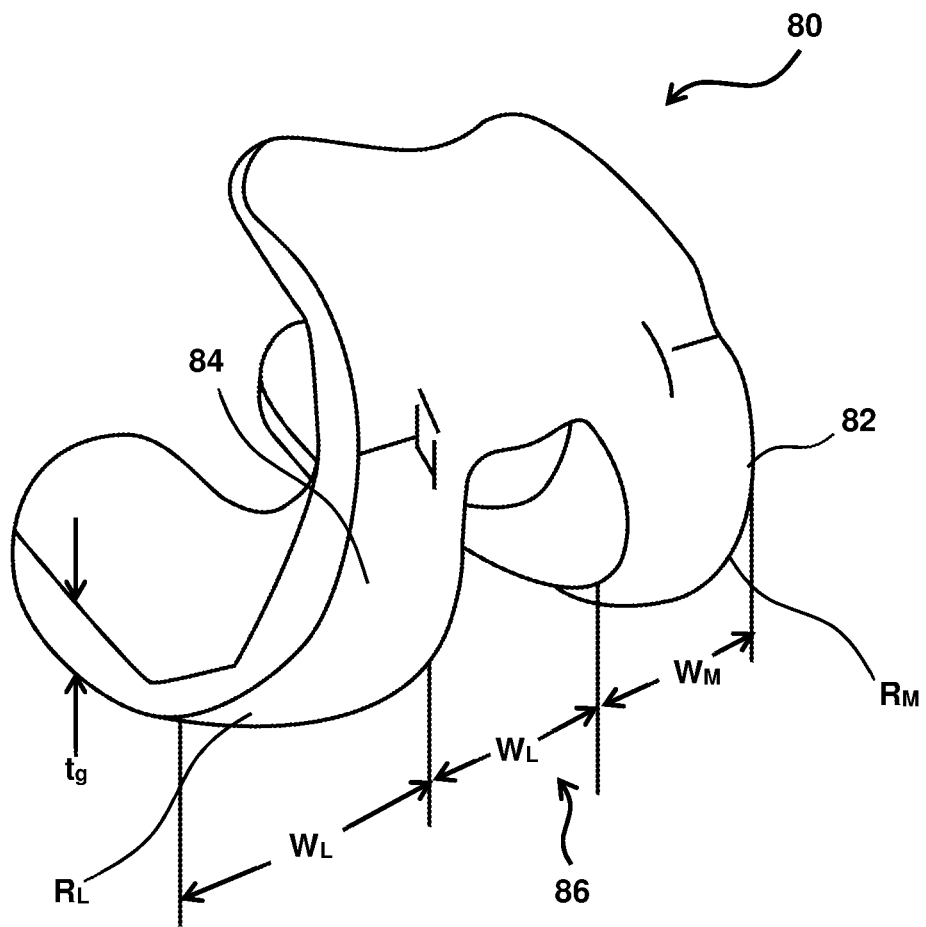
FIG. 7 depicts an another exemplary femoral component of a prosthetic knee joint.

Referring to FIG. 7, another femoral component 80 of a knee joint implant of the present invention is provided. The femoral component 80 includes medial and lateral condyle portions 82 and 84. The medial condyle portion 82 has a width Wm and a radius $R_m$ and the lateral condyle portion 84 has a width $W_L$ and a radius $R_L$, wherein the width $W_m$ and $W_L$ can be of equal dimension, or in the alternative, the widths $W_m$ and $W_L$ can be of non-equal dimension. Similarly, the medial and lateral condyle portions 82 and 84 radii $R_m$ and $R_L$ can be of equal dimension, or in the alternative, radii $R_m$ and $R_L$ can be of non-equal dimension. In this regard, the size differences between the widths and/or radii of the medial and lateral condyle portions can be at least 5 percent, 10 percent, or 20 percent. A trochlear groove 86 is disposed between the medial and lateral condyle portions 82 and 84 and has a width $W_1$.

In this manner, the widths $W_m$ and $W_L$ and the radii $R_m$ and $R_L$ of the femoral components 80 can be provided in a range of sizes to more precisely emulate the size and dimensions of a male or female human knee joints. For example, the radii $R_m$ and $R_L$ of the medial and lateral portions 82 and 84 of the femoral component 80 can be selected such that the radius Rm of the medial condyle portion is larger with respect to the radius $R_L$ of the lateral condyle portion. As such, the radii $R_m$ and $R_L$ of the medial and lateral portions 82 and 84 form a substantially partial conical surface. Additionally, the thickness t3 and the material densities of the femoral components 80 are selected to correspond to male or female bone thickness and densities.

As previously discussed, a male femoral component will generally have greater widths $W_m$ and $W_L$ and the radii $R_m$ and $R_L$, thus bearing surface areas, than that of a comparable female femoral component widths $W_m$ and $W_L$ and the radii $R_m$ and $R_L$, Similarly, the male femoral component will generally have a greater material thickness t3 than that of thickness of a comparable female femoral component. Thus, a "large" size for a male prosthetic knee joint may differ significantly in size, proportion, and construction from a large-sized prosthetic knee joint for women. Furthermore, as shown in FIG. 5, an upper section of the female femoral component can be generally narrower than that of a comparably sized male femoral component to accommodate structural differences between the female and male femurs. In other words a female femoral component design can have scalloped edges compared to the male femoral component design. Additionally, the thickness, the material densities, and the material composition of the femoral components may be selected to correspond to different male and female bone thickness and densities. Additional dimensions of the femoral portion of the knee joint can be utilized in the design and configuration of the femoral components.

Figure 8:
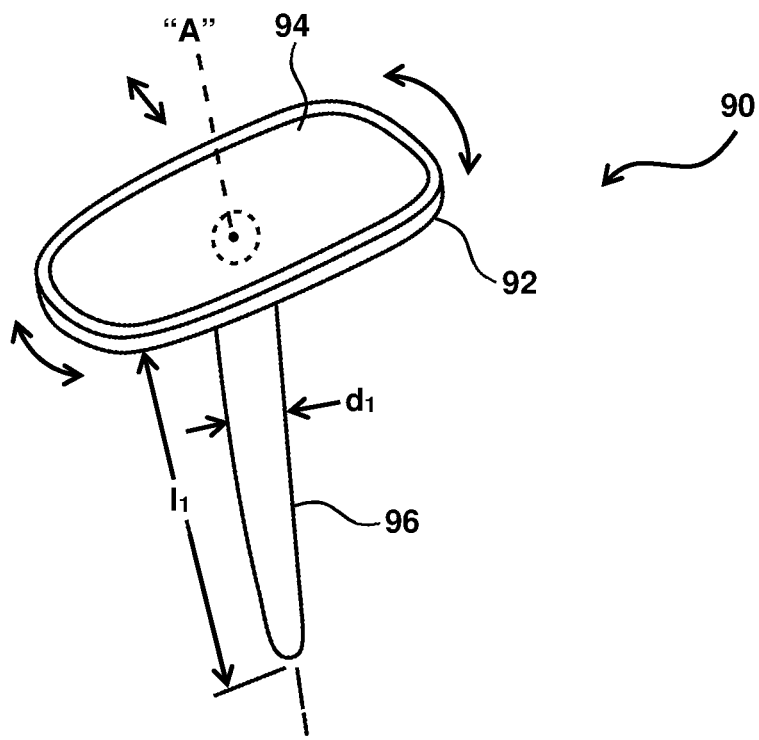
FIG. 8 depicts an exemplary rotatable tibial component of a prosthetic knee joint.

Referring to FIG. 8, a tibial component 90 of a knee joint of the present invention is provided. The tibial component 90 includes a platform 92, having a substantially oval shape, wherein a cushioning material 94 replaces the medial and lateral meniscus 24 and 26. A bone spike 96 is included for insertion into the prepared end of the tibia, securing the tibial component 90 to the tibia. The bone spike 96 can be substantially conical in shape, having a maximum diameter $d_1$ and length $l_1$. The platform 92 can be rotatably connected to the bone spike 96, such that the platform 92 can rotated with respect to the central longitudinal axis "A" of the bone spike 96.

Figure 9:
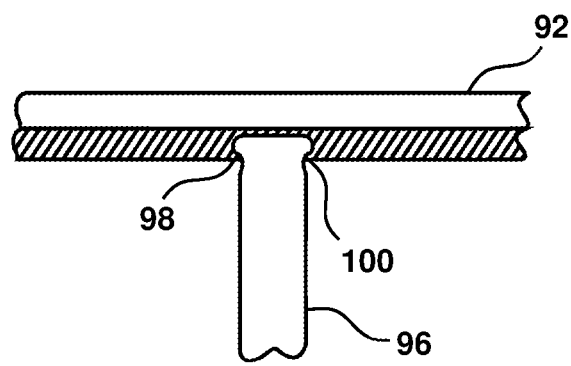
FIG. 9 depicts a partial cross section of the rotatable tibial component of FIG. 8.

In an embodiment as shown in FIG. 9, the platform 92 includes a slotted section 98, in which a head portion 100 of the bone spike 96 is positioned. The slotted section 98 is configured to capture the head portion 100 of the bone spike 96, securing the head portion 100 within the slotted section 98, yet allowing the platform 92 to rotate with respect with the bone spike 96. In this manner, the platform 92 can rotate with respect to a femoral component as the knee joint is moved between flexion and extension, thereby decreasing the frictional forces between the contacting surfaces of the femoral component and a cushioning material of the platform 92. Furthermore, the rotation of the platform 92 can decrease the stresses provided on the implant/bone interface, decreasing the likelihood of failure and increasing the life expectancy of the implant. It is contemplated that the other rotational, translation, and positional configurations of the platform 92 with respect to the bone spike 96 can be provided to further increase the efficiency of emulating a natural knee joint and accounting for the anatomical differences between male and female joints.

Figure 10:
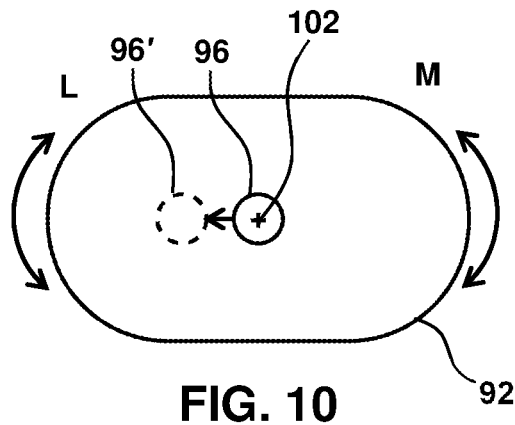
FIG. 10 depicts a platform of a rotatable tibial component of a prosthetic knee joint.

Referring to FIG. 10, the bone spike 96 can be centrally positioned on the flat platform 92, such that the center 102 of the platform 92 is aligned along the central longitudinal axis of the bone spike 96. Alternatively, the bone spike 96' can be positioned offset from the center 102 of the platform 92, such that the center 102 of the platform 92 is rotatable about the bone spike 96'.

Figure 11:
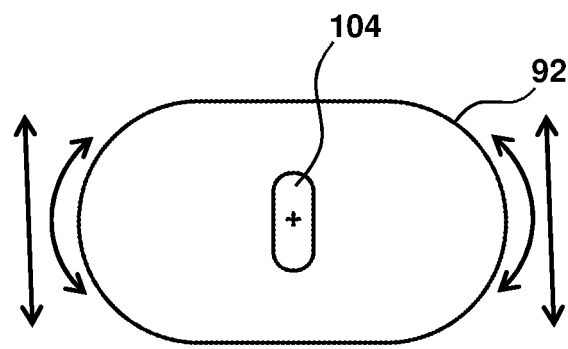
FIG. 11 depicts a platform of a rotatable/translatable tibial component of a prosthetic knee joint.

Referring to FIG. 11, the platform 92 can include an elongated slotted section 104, such that the platform 92 can slide in the anterior and posterior directions as the knee joint is moved between flexion and extension. In addition, the platform 92 can rotate with respect to the bone spike 96 as the knee joint is moved between flexion and extension. In this manner, the compound movement for the platform 92 can be used to emulate high flexion.

Figure 12:
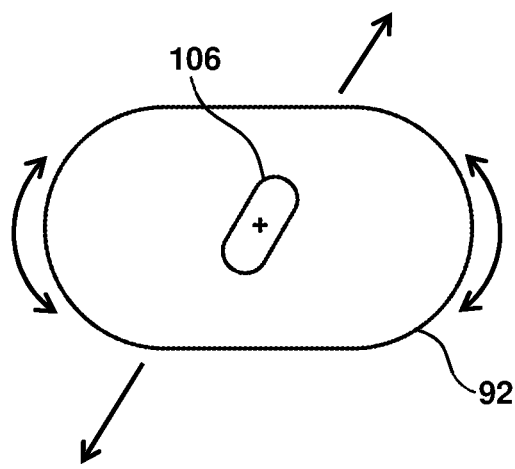
FIG. 12 depicts another platform of a rotatable/translatable tibial component of a prosthetic knee joint.

Referring to FIG. 12, the platform 92 includes an angular elongated slotted section 106, such that the platform 92 can slide substantially in the anterior/posterior and medial/lateral directions as the knee joint is moved between flexion and extension. In addition, the platform 92 can rotate with respect to the bone spike 96 as the knee joint is moved between flexion and extension.

Similar to the femoral components, the tibial components 90 are designed and configured for use in replacement of the knee joint in males and females. The dimensions of the tibial components once again may be provided in a range of sizes to span the normal size ranges of male and female human knee joints. As showing in FIGS. 4 and 6, the male platform 50 has a substantially oval shape, whereas the female platform 72 has an elongated oval shape. The shapes of the platforms 50 and 72 are selected to accommodate the differences in sizes and bearing surface areas of the corresponding male and female femoral components 48 and 60. Additionally, the thickness and the material densities of the tibial components are selected to correspond to or function with male and female bone thickness, densities, geometry, range of motion, or the like. Furthermore, additional dimensions of the tibial portion of the knee joint can be utilized in the design and configuration of the tibial component 90.

Figure 13:
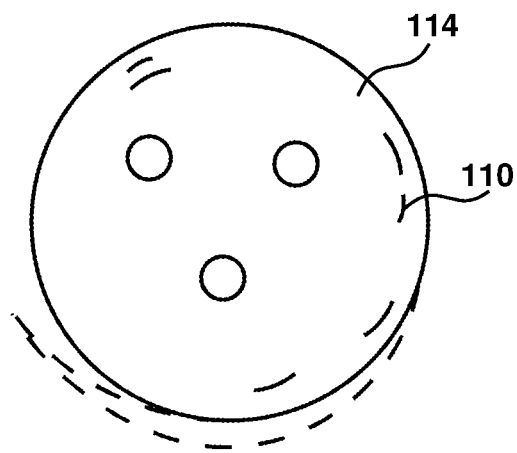
FIG. 13 depicts an exemplary male patella with pegs or contact points arranged based on the male anatomy.
Figure 14:
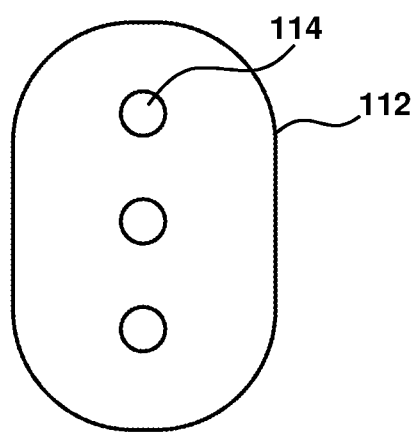
FIG. 14 depicts an exemplary female patella with pegs or contact points arranged based on the female anatomy.

Referring to FIGS. 13 and 14, a male patella 110 and a female patella 112 are provided. As shown in these figures, the male and female patellas 110 and 112 have substantially different shapes, where the female patella 112 is more elongated with respect to the male patella 110. As such, when replacement patellas are provided, they are provided in accordance with the gender of the patient.

Furthermore, in surgical procedures requiring resurfacing of the patella surfaces, contact pegs 114 can be affixed to the surface, providing multiple point contact surfaces between the patella and the femur or femoral implant. As male and female patellas 110 and 112 have different shapes, the arrangement of the pegs 114 can be changed accordingly. As shown in FIG. 13, the pegs 114 are positioned in a substantially triangular configuration for the male patella, allowing for the wider surface of the male patella 110. As shown in FIG. 14, the pegs 114 are positioned in a substantially linear configuration, allowing for the more linear surface of the female patella 114. Providing such contact pegs (rather than replacing or resurfacing the entire patella) offers a number of advantages, which include greater applicability to minimally invasive procedures, reduced articulating surface area, etc. Published U.S. Patent Application Publication No. US 2003/0028196 A1 discloses a number of such pegs or reduced bearing surface implants that can be used with the present invention. The entire content of this patent application is incorporated herein by reference.

Although FIGS. 2-14, show total knee replacement components, the present invention is well-suited for partial knee replacement components such as uni-compartmental and bi-compartmental implants. The present invention also contemplates the use for re-surfacing and surface bearing procedures and/or components.

Figure 15:
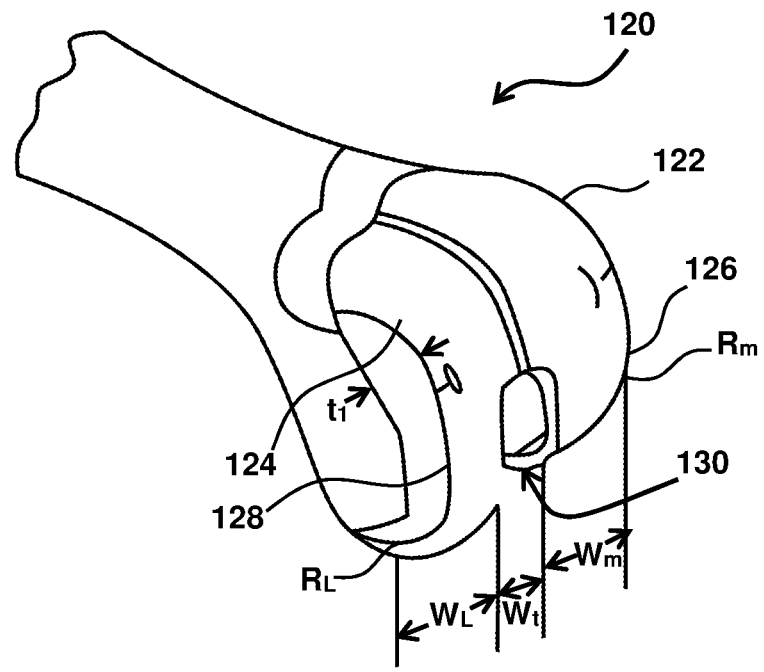
FIG. 15 depicts an exemplary bi-compartmental femoral component of a male prosthetic knee joint.

Referring to FIG. 15, a bi-compartmental male femoral component 120 of a knee joint implant of the present invention is provided. The femoral component 120 includes medial and lateral components 122 and 124. The medial component 122 includes a medial condyle portion 126 having a width $W_m$ and a radius $R_m$. The lateral component 124 includes a lateral condyle portion 128 having a width $W_L$ and a radius $R_L$. As previously discussed, the widths $W_m$ and $W_L$ can be of equal dimension or can be of different dimensions. Similarly, the medial and lateral condyle portions 126 and 128 radii $R_m$ and $R_L$ can be of equal dimension or can be of non-equal dimension. A trochlear groove 130 formed by the combination of the medial and lateral components 122 and 124 is disposed between the medial and lateral condyle portions 126 and 128 and has a width $W_t$.

Figure 16:
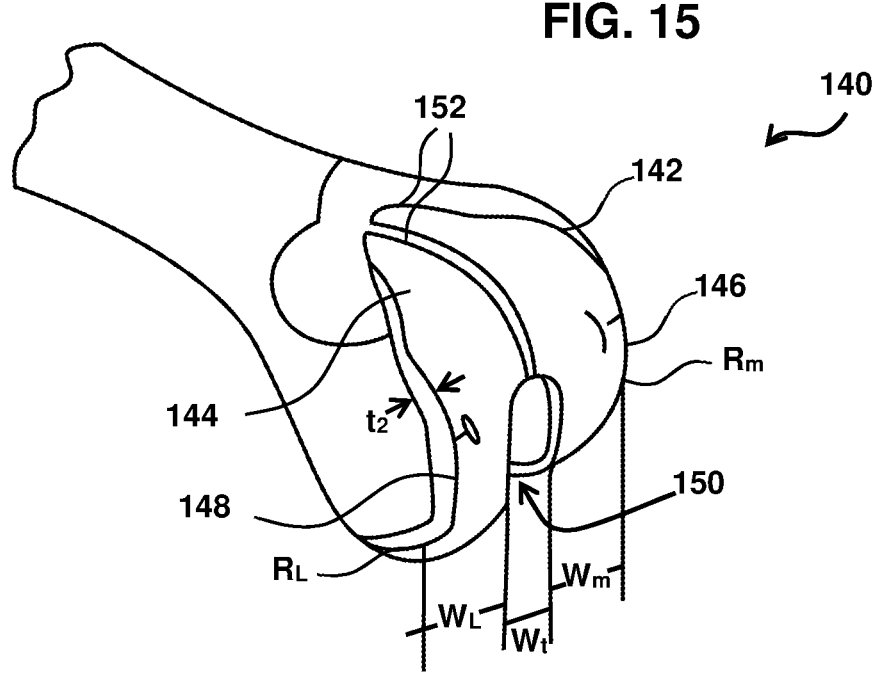
FIG. 16 depicts an exemplary bi-compartmental femoral component of a female prosthetic knee joint.

Referring to FIG. 16, a bi-compartmental female femoral component 140 of a knee joint implant of the present invention is provided. The femoral component 140 includes medial and lateral components 142 and 144. The medial component 142 includes a medial condyle portion 146 having a width $W_m$ and a radius $R_m$. The lateral component 144 includes a lateral condyle portion 148 having a width $W_L$ and a radius $R_L$. As previously discussed, the widths $W_m$ and $W_L$ can be of equal dimension or can be of different dimensions. Similarly, the medial and lateral condyle portions 146 and 148 radii $R_m$ and $R_L$ can be of equal dimension or can be of different dimensions. A trochlear groove 150 formed by the combination of the medial and lateral components 142 and 144 is disposed between the medial and lateral condyle portions 146 and 148 and has a width $W_t$. The widths $W_m$ and $W_L$ and the radii $R_m$ and $R_L$ of the medial and lateral components 132 and 134 are provided in a range of sizes to span the normal size ranges of female human knee joints. Additionally, the thickness $t_2$ and the material densities of the medial and lateral components 132 and 134 are selected to correspond to female bone thickness and densities.

As previously discussed, male femoral components will generally have greater widths $W_m$ and $W_L$ and radii $R_m$ and $R_L$, thus bearing surface area, than that of comparable female femoral components widths $W_m$ and $W_L$ and radii $R_m$ and $R_L$. Similarly, the male femoral components will generally have a greater material thickness $t_1$ than that of thickness of a comparable female femoral component. Thus, a "large" size for a male prosthetic knee joint may differ significantly in size, proportion, and construction from a large-sized prosthetic knee joint for women. Furthermore, as shown in FIGS. 15 and 16, an upper section 152 of the female femoral components 142 and 144 can be generally narrower than that of a comparably male femoral components 122 and 124, to accommodate structural differences between the female and male femurs. In other words, the upper section 152 is such that the female femoral components 142 and 144 have scalloped edges compared to the male femoral components 122 and 124. Additionally, the thickness, the material densities, and the material composition of the femoral components 122, 124, 142, and 144 may be selected to correspond to different male and female bone thickness and densities. Additional dimensions of the femoral portion of the knee joint can be utilized in the design and configuration of the femoral components 142 and 144.

Thus, a gender-specific design may be identified by one component having less material than for the opposite sex. Furthermore, additional dimensions of the femoral portion of the knee joint can be utilized in the design and configuration of the femoral components. One or more of these dimensions may be varied so that an implant is better suited to a male or female patient. Thus, an implant design may be considered gender-specific if one or more of these parameters has been selected to better match either a male or female.

A gender-specific prosthetic design may also be identified by comparing relative differences that exist between a female design and a male design. For example, if one or more dimensions (e.g., bearing surface area, widths, radii, curvature, thickness of material, amount of metal, range of motion, flexibility, etc.) or relative proportions (e.g., relative width or relative differences in angles, minimum or maximum sizes, etc.) or an implant design for one sex varies by more than 5 percent, or alternatively by 10 percent or more, or even by about 20 percent or more, from an implant designed for the opposite sex, then the design may qualify as being gender-specific.

Figure 17:
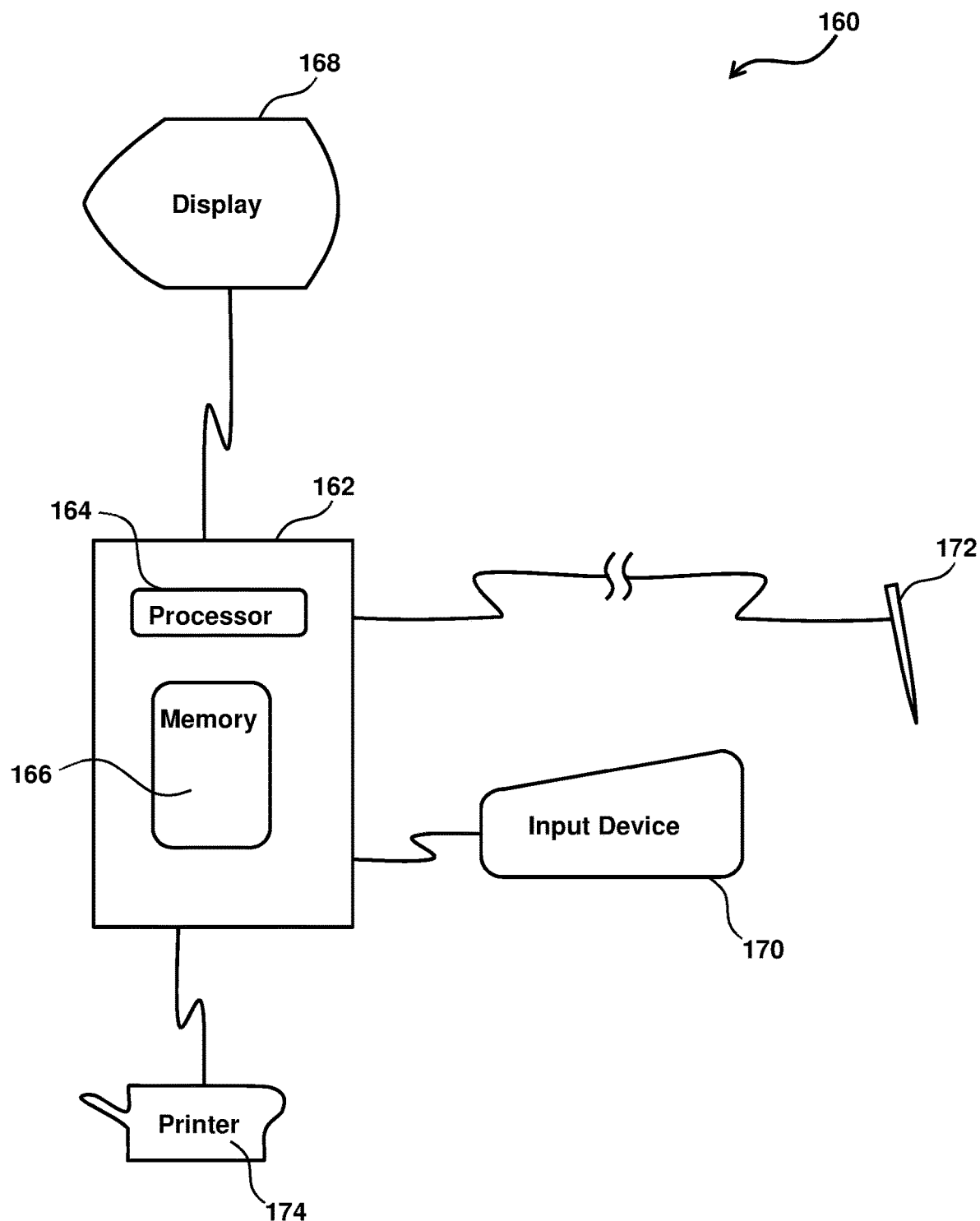
FIG. 17 depicts a schematic diagram of a computer navigation system of the present invention.

Referring to FIG. 17, a computer navigation system 160 of the present invention is provided and schematically shown. The computer navigation system 160 includes a central processing unit (CPU) 162, having a processor 164 and memory 166, a display device 168, and input devices, including a keyboard 170 and a stylus 172. A computer program is stored on the CPU 162, where the computer program can be used to aid in the selection, preparation, and insertion of implants into a patient. The stylus 172 can be used to provide single point locations or multiple point locations to outline the contours of a surface of a portion of a joint. The navigation system 160 can further include a printer 174.

An anatomical database is stored on the CPU 162 and is accessible by the computer program to determine appropriate implants for use in the patient. In an embodiment, the anatomical database includes information relating to a joint in the body of a patient, for example a knee joint. The anatomical database includes a library of joint mappings, having a broad range of joint sizes, as well as including information relating to gender differences in the joints. For example, the anatomical database can include information on bone thickness, density, the radii of the medial and lateral condyles, the widths of the medial and lateral condyles, the width of the trochlear groove, and the angular relationship of the medial and lateral condyles with respect to the central longitudinal axis of the femur for a broad range of different size joints for male and females. In other words, conventional computer navigation systems include a library or database of anatomical parameters that are used in the registration or other calibrating process, but the anatomical parameters are based on a unisex model that represents a composite of male and female anatomies. In contrast, the computer navigation system of the present invention includes a male library or database and a female library or database. The separate libraries or databases include differences in the anatomy. Exemplary differences have been discussed previously and additional gender differences are described below. Thus, with the computer navigation system of the present invention, the patient's gender is selected and the appropriate library or database is used in the registration or other calibrating process.

Figure 18:
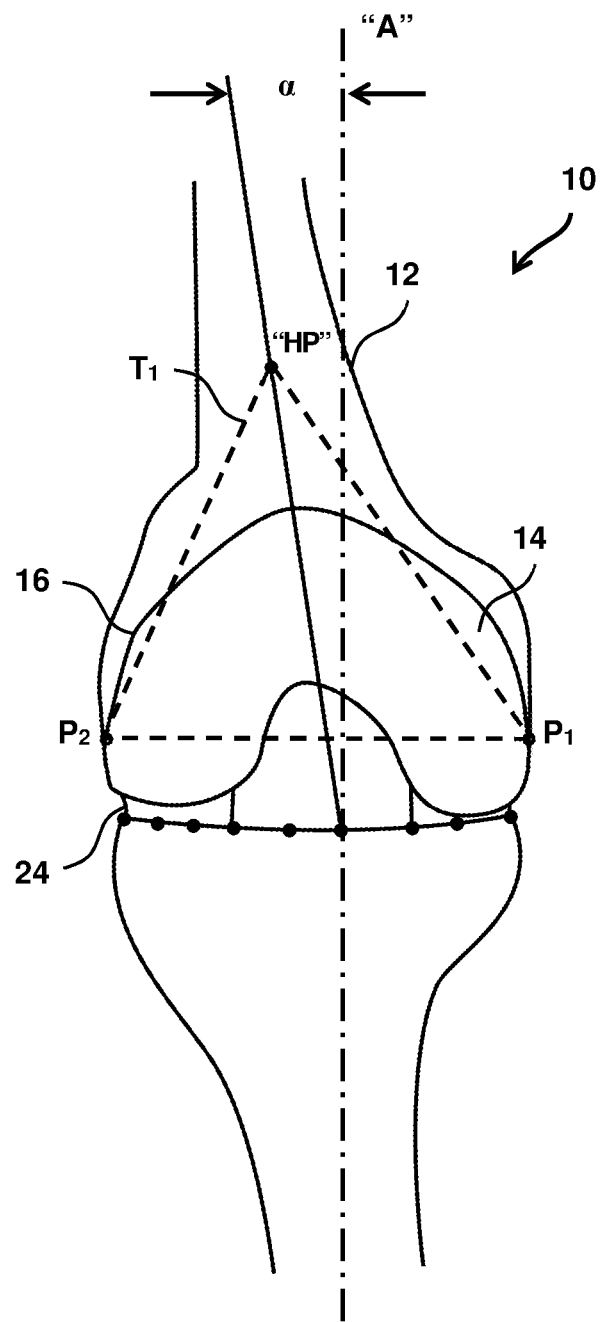
FIG. 18 depicts a triangular mapping of a femur portion of a knee joint.

In a method of use, the stylus 172 is used to the map the joint, with at least three points located on the joint to determine the anatomical parameters of the joint. The joint mapping is displayed on the display device 168. Referring to FIG. 18, in a knee joint 10 the stylus 172 maps the femoral portion 12 of the knee joint 10. The stylus 172 is used to locate a home point "HP" on the femur 12, where the home point lies on the top surface on the femur 10 in a plane defined by the central longitudinal axis "A" of the femur 10. At least two additional points "$P_1$" and "$P_2$" are located with respect to the home point, such as end surfaces of the medial and lateral condyles 14 and 16. The three points (HP, $P_1$ and $P_2$) define a triangular mapping "$T_1$" of the femoral portion 12 of the knee joint 10, which is displayed on the display device 168. In addition to the triangular mapping, gender information is also provided.

In an alternative embodiment, the display device 168 displays a generic knee joint, highlighting a point on the joint to be located using the stylus 172. For example, a home point "HP" and the end surfaces of the medial and lateral condyles are highlighted on the generic knee joint. The stylus 172 is utilized to locate the corresponding points on the knee joint 10 of the patient.

The computer program utilizes the mapped points and the gender information to provide a preliminary model for the femoral portion 12, which is displayed on the display device 168. The preliminary model is based on a statistical analyzing of the relationship of the mapped points and the gender information, in comparison to the knee joint database. The resulting preliminary model can include information on the radii of the medial and lateral condyles, the widths of the medial and lateral condyles, the width of the trochlear groove, and the angular relationship of the medial and lateral condyles with respect to the central longitudinal axis of the femur. Based on the preliminary model an appropriately size femoral implant can be selected for use, as well as a corresponding cutting pattern for that implant.

The above system has been described as using three points to provide a triangular mapping. However, it is understood that additional information can be utilized to provide a more refined model of the femoral portion 12 of the knee joint 10. For examples, the input device 170 can be used to map anterior and posterior points of the medial and lateral condyles, the femoral contacting surface of the medial and lateral condyles, the trochlear groove, etc. Additional information, such as the bone diameter and angular relationship between the femur and the pelvis can be utilized to refine the model.

Figure 19:
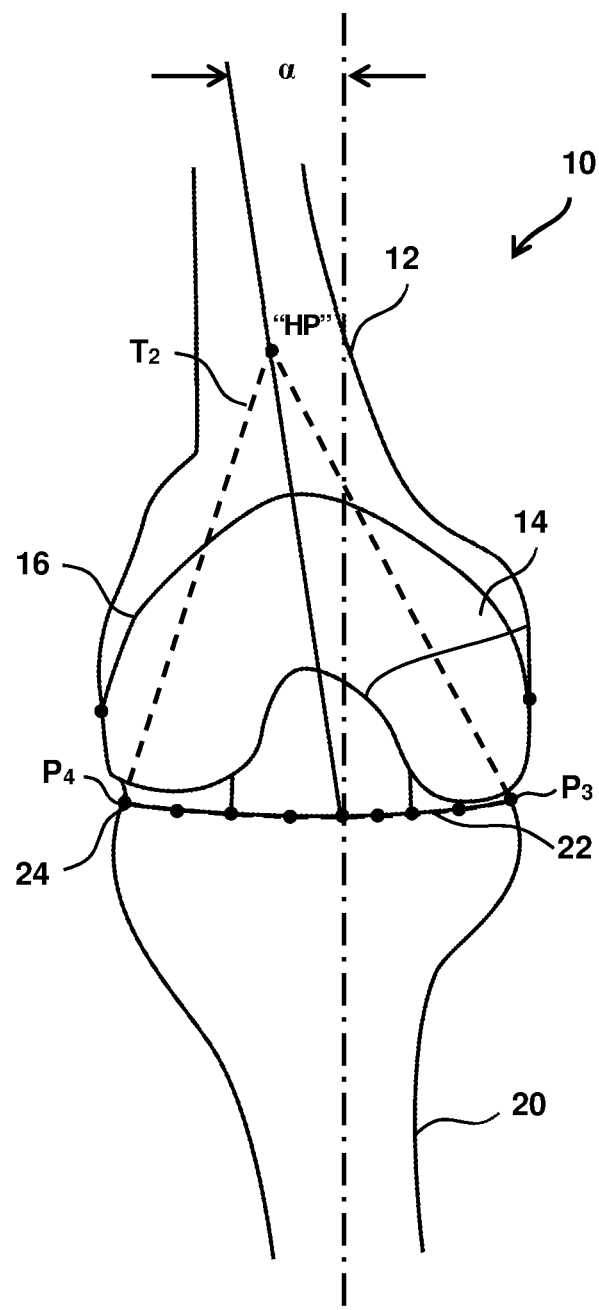
FIG. 19 depicts a triangular mapping of a tibia portion of a knee joint.

Referring to FIG. 19, in a similar method, the computer navigation system 160 can be used to map the tibial portion 20 of the knee joint 10. The stylus 172 is used to locate reference points on the end portion of the tibia 20 with respect to the home point "HP" on the femur 12. For example, the stylus 172 can be used to map points along the tibial plateau 22, including the tibial plateau end points $P_3$ and $P_4$, to providing a triangular model "$T_2$" of the tibia 20 as well as the angular relationship "a" between the tibia 20 and femur 12.

The computer program utilizes the mapped points and the gender information to provide a preliminary model for the tibial portion 20, which is displayed on the display device 168. The tibial portion 20 can be displayed either individually or in relation to the femoral portion 12. The resulting preliminary model can be used to select an appropriately sized tibial implant, as well as a corresponding cutting pattern for that implant. The selection of the femoral and tibial implants is not only based on the inputted data, by also on the implants themselves, and their ability to function appropriately together.

Other gender-specific differences may be used to further customize a medical implant such as a prosthetic knee for men or women. For instance, surfaces of the device may have different ingrowth surfaces, porosity, HA, or BMP coated or bonded to it.

In addition to the knee joint, additional prosthetic implants can be designed and configured for gender specific use. For example, as noted above, the female pelvis is distinguished from that of the male by its bones being more delicate and shallower in depth. The ilia of the female pelvis are less sloped, and the anterior iliac spines more widely separated; hence the greater lateral prominence of the hips in females. The superior aperture of the lesser pelvis is larger in the female than in the male; it is more nearly circular, and its obliquity is greater. The inferior aperture is larger and the coccyx more movable. The sciatic notches are wider and shallower, and the spines of the ischia project less inward. The ischial tuberosities and the acetabula are wider apart, and the former are more everted. The pubic symphysis is less deep, and the pubic arch is wider and more rounded than in the male, where it is an angle rather than an arch.

Because of the differences between the male pelvis and the female pelvis, hip configuration and alignment differ between the genders. Such differences require differing implant configurations. In accordance with the present invention, prosthetic hip implants may be designed and configured for gender specific use, taking into account the structural differences between the female and male pelvis and connecting femurs.

Thus, another example of where the present invention may be used to improve currently available implant designs is in treatment of injuries to the pelvis or hip. As mentioned above, an implant designed for women may be designed to provide greater range of motion than a similar implant designed for men. Females often benefit from having a greater range of motion for hips just as they do for knees. Thus, the female design may be more flexible in the acetabular component, more flexible in the femoral stem, or have a greater modulus of elasticity (especially in more osteoporotic bone). Designing the female prosthetic so that the femoral head contacts a thinner acetabulum also may change range of motion and stability to be more suitable for women than men.

Additionally, the offset for the femoral head and neck region may be different for men than women. For example, a female design may have less offset while a male design may have a greater offset to increase the lever arm. The difference in offset may be about 5 percent or greater in one embodiment, although as described above the offset may differ by 10 percent or more, or by 20 percent or more.

Another way in which prosthetic designs such as the hip may incorporate gender-specific features is with the use of different ingrowth surfaces. For example, the superior portion under compression on the acetabular component may have HA coating and/or a roughened surface texture for one gender while less or no HA coating and/or a smoother surface texture for the opposite gender. Likewise, the inferior coating may be porous or fiber metal coating or porous tantalum coating so that there would be two or more ingrowth surfaces on the same gender-specific implant.

Since it may be difficult to immediately recognize some of these gender-specific design differences, one or more components may be color-coded so that they may be more readily identified by visual inspection. For example, the rotating or bearing surface of the femoral head may have one color for women and another color for men. Thus, a component having a pink visible surface may signify that the gender-specific design of the implant is for women, while a black surface may signify that the gender-specific design is for men. This color-coding of one or more components may be used in place of or in conjunction with any other gender identification systems, including those described elsewhere herein.

It is further contemplated the gender specific prosthetic implants can be designed and configured for use in the any joint in a body, including ankle, knee, hip, spine, neck, wrist, elbow, and shoulder. In spine treatment, for example, a nucleus pulposes implant for women may have greater elasticity or greater hydrophilic capability. Likewise for spinal implants, the shape, angle, or distance distracted between the disc space may be designed to be gender-specific for men and women. In addition, disc replacement technology may have gender-specific features such as differences in disc height or angulation changes such as lordosis or rotational angle. Likewise, a spinal cage could have gender-specific designs that vary in thickness or forced expansion.

Bone cement, such as used in spine treatment or in treating other bones in the body, also may have a different viscosity for men and women, different rates of introduction into the body, or different amounts of bonding or interdigitation, especially with osteoporotic bone in females versus males.

The use of gender-specific designs also may result in kits of implants, tools and devices tailored primarily for a particular gender. For instance, a kit of implants of varying sizes intended for women may have a generally smaller size than a kit of similar implants intended for men. Providing a gender-specific kit allows for the reduction or elimination of conventional kit components that might primarily be intended for use on the opposite sex. Likewise, there may be differences in the tools and instruments provided in one kit versus another due to anatomical, physiological, or other differences between men and women. One benefit of providing gender-specific kits is that it may reduce the amount of variety of devices and instruments that may be prepared for a particular surgery. The potential reduction in complexity and number of devices and instrumentation may in turn allow a physician to perform surgeries more efficiently and successfully.

Sutures also may be designed to have gender-specific features. Today, suture materials are all designed to have the same properties for men and women. Under the present invention, however, suture material may have greater elasticity for females than for males.

Stents are another example where a currently unisex approach could be improved by taking into account gender-specific differences. Stents are used in a wide variety of applications, such as for aneurysms, aortic, cardiac, carotid, vascular anastomosis, vascular angioplasty, and the like. As is well known stents are typically inserted in a compressed state and then expanded when in position. The expansion of stents today is the same for men and women; yet female vessel tissue tends to be more elastic than in men. Therefore, it is believed the vessels in women would apply a less resistance to an opening stent than in men. While this difference is not currently taken into account, one embodiment of the present invention would be to design a stent to require a lower opening force for women than a stent designed for men. For example, a balloon used to expand a male designed stent may apply a greater opening force than a balloon used to expand a female designed stent.

Furthermore, stent expansion may involve less elasticity and greater stiffness in men than in women since male vessel tissue is generally more rigid than for women. Since female tissue often is more pliable, a female stent design may have a lower modulus of elasticity to expand, may be more elastic, and less rigid. In addition, a male stent design may have differences in drug release than in women. For example, a male stent design may have a greater drug release associated with it, may have specific localized drug release, or a greater concentration of drug released over a shorter period. Additionally, different drug combinations may be associated with a male stent design than for a female stent design. The stent may have multiple layers for providing different drug deliveries for men and women. For example, one layer may be porous or permeable that allows a drug to be released from an inner coating or layer. The porous or permeable coating or layer may have different apertures for men than for women, thereby providing a gender-specific drug delivery. In addition, the coatings or layers may react differently to temperature, pH, or other differences in the intended environment that may be present between men and women. For example, a porous or permeable layer may have an outer coating that dissolves when deployed in a female, thereby allowing the inner coating or layer to be released into the body, but remains substantially intact during exposure in a male body. Alternatively, the outer coating may have a different rate of degradation for men than women, thereby allowing for gender-specific rates of drug delivery.

Figure 20:
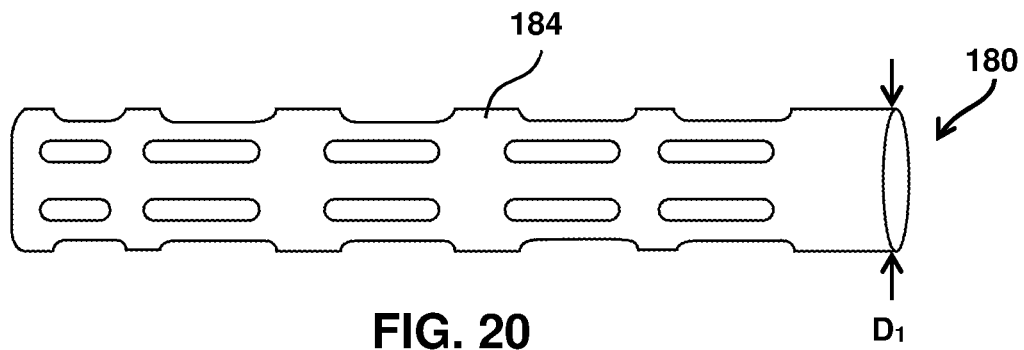
FIG. 20 depicts an exemplary vascular stent.

FIG. 20 illustrates an embodiment of the invention concerning an arterial stent 180. Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis. Stents also can be used to provide primary compression to a stenosis in cases in which no initial PTCA or PTA procedure is performed. While stents are most often used in the procedures mentioned above, they also can be implanted on another body lumen such as the carotid arteries, peripheral vessels, urethra, esophagus and bile duct.

In typical PTCA procedures, a guiding catheter or sheath is percutaneously introduced into the cardiovascular system of a patient through the femoral arteries and advanced through the vasculature until the distal end of the guiding catheter is in the aorta. A guidewire and a dilatation catheter having a balloon on the distal end are introduced through the guiding catheter with the dilatation catheter sliding over the guidewire. The guidewire is first advanced out of the guiding catheter into the patient's vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size, such as with a radiopaque liquid, at relatively high pressure to displace the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. Stents are generally cylindrically shaped devices which function to hold open and sometimes expand a segment of a blood vessel or other arterial lumen, such as a coronary artery. Stents are delivered in a radially compressed condition to the target location and then are deployed into an expanded condition to support the vessel and help maintain it in an open position. In one embodiment, the stent may be a self-expanding type formed from, for example, shape memory metals or super-elastic nickel-titanium (NiTi) alloys, which will automatically expand from a compressed state when the stent is advanced out of the distal end of the delivery catheter into the body lumen.

Physiological differences between the female and male genders may also be found in the cardiovascular systems of men and women. For example, women, on average, have smaller diameter and thinner-walled arteries than men. The invention accounts for these physiological differences by providing different stent designs for men and women. Thus, the invention provides stents 180 that are configured and dimensioned for gender specific use. As noted above, upon insertion into an artery, the stent 180 expands from an initial, compact condition to an expanded condition having a diameter $D_1$, wherein the rate of expansion E is dependent on the material properties of the stent 180. In the expanded condition, the diameter $D_1$ is of sufficient size to impart an expansive force Fe onto the inner arterial wall.

In a first embodiment, the stent 180 is designed and configured for use in angioplasty procedures in males. One or more stents 180 may be provided having at least one rate of expansion E and at least one expanded diameter $D_1$ configured and dimensioned to span the normal size ranges of male human arteries. Additionally, the expansive force Fe imparted onto the inner arterial wall is a function of the arterial wall thickness, such that the expansive force Fe is of sufficient strength to maintain the artery in an open condition preventing reclosure, without damage to the inner arterial wall. Furthermore, additional dimensions of the arteries can be utilized in the design and configuration of the stent 180.

Figure 21:
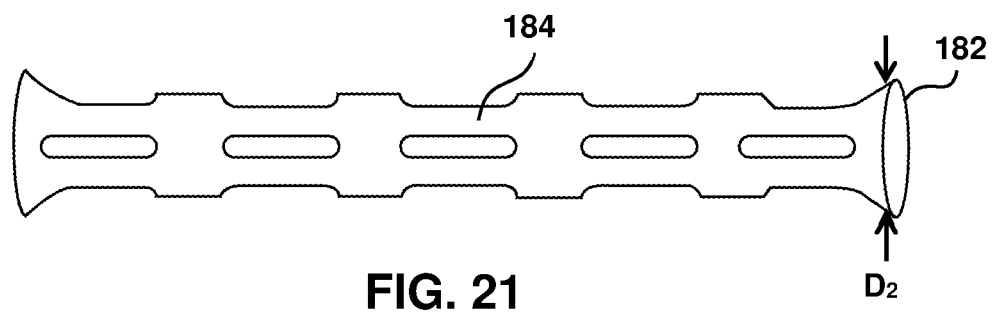
FIG. 21 depicts an exemplary female vascular stent.

In a second embodiment, shown in FIG. 21, the stent 182 is designed and configured for use in angioplasty procedures in females. Once again, one or more stents 182 may be provided having at least one rate of expansion E and at least one expanded diameter D2 configured and dimensioned to span the normal size ranges of female human arteries. Additionally, the expansive force Fe imparted onto the inner arterial wall is a function of the arterial wall thickness, such that the expansive force is of sufficient strength to maintain the artery in an open condition preventing reclosure, without damage to the inner arterial wall. Furthermore, additional dimensions, gender-specific features, or other parameters of the arteries can be utilized in the designed and configuration of the gender specific stent 182. For instance, the stent 82 also may account for the effect of an illness or medical condition on the strength, size, or thickness of a vessel or vessel wall, which optionally may also be dependent at least in part upon gender. Some of the structural features of the stents that account for gender-specific differences include the following: stent 182 has ends that flare outwardly, while stent 80 is substantially cylindrical; stent 182 has fewer openings than stent 180; and the openings in the sidewall of stent 182 are generally larger than the openings in the sidewall of stent 180.

Figure 22:
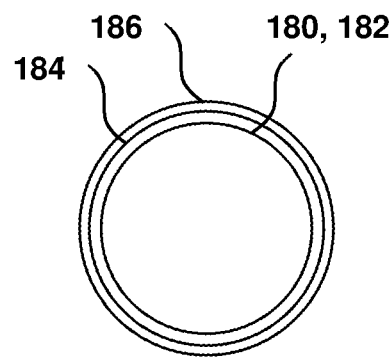
FIG. 22 depicts a cross sectional view of an embodiment of the stent of FIG. 20.

As discussed above, coatings can be used to make stent designs genderspecific. It is well known that the stents 180 and 182 can be coated with a pharmaceutical agent 184. As shown in FIG. 22, the pharmaceutical agent 184 can be combined with a coating 186 or other medium used for controlled release rates of the pharmaceutical agent 184. The pharmaceutical agent 184 can be incorporated into or covered by a monolithic layer or coating, wherein the agent 184 diffuses through the coating 186 and is released into the surrounding fluid. Alternatively, the coating 186 can be a degradable coating, such that as the coating 186 degrades the pharmaceutical agent 184 is released.

The pharmaceutical agent 184 can be a drug used for the prevention or treatment of restenosis. Formulations useful for restenosis prevention or treatment can include, but are not limited to, heparin and heparin fragments, colchicine, taxol, agiotensin converting enzyme (ACE) inhibitors, angiopeptin, Cyclosporin A, goat-anti-rabbit PDGF antibody, terbinafine, trapidil, interferon-gamma, steroids, ionizing radiation, fusion toxins, antisense oligonucleotides, gene vectors, and rapamycin.

In addition to or as an alternative to, the pharmaceutical agent 184 may be a therapeutic biologic agent. Examples of such agents include, but are not limited to, hormones, cells, fetal cells, stem cells, bone morphogenic proteins (BMPs), tissue inductive factors, enzymes, proteins, RNA, viruses, etc.

As previously discussed, men and women may metabolize some medications at different rates and react differently to different types of medications. Just as the size, shape, and other performance characteristics of a stent may be tailored or customized primarily for a particular gender, the pharmaceutical agents used with the stents also may be tailored primarily for a particular gender. Thus, one embodiment of the invention provides a coated stents 180, 182 where the coating is formulated differently for different genders.

It should be noted that customizations of devices or treatments according to the invention may be used individually or in combination with other embodiments described herein or variations thereto. For instance, a single stent construction used for both men and women may have different coatings intended primarily for different genders. In addition, however, different coatings may also be used on different stent constructions that are designed primarily for a particular gender.

In one embodiment using a pharmaceutical agent 184 coated onto the stent 180, 182, the pharmaceutical agent 184 release rate and dosage are selected to correspond to expected male metabolization and reactions. A coating 186 may also be provided on the stent 180, 182 so that the pharmaceutical agent 184 is covered by or incorporated into the coating 186. The coating 186 may be used to control the timing and release rate of the pharmaceutical agent 184. For example, the pharmaceutical agent 184 may be released gradually through diffusion through the coating 184 or after at least partial degradation of the coating 186. In this manner, the coating 186 can be designed and configured to release the pharmaceutical agent 184 at a rate and dosage corresponding to metabolization and potential reactions of primarily either men or women.

Similarly, the pharmaceutical agent 184 release rate and dosage may be selected to correspond to expected female metabolization and reactions in the same manner.

While in the foregoing a stent 180, 182 was depicted, in other embodiments, similar techniques may be used to coat other types of implantable medical devices, such as hip and knee replacements (total and partial), spinal implants, scaffolds, biological implants or grafts, tissue grafts, screws, plates, rods, prosthetic devices, etc.

Figure 23:
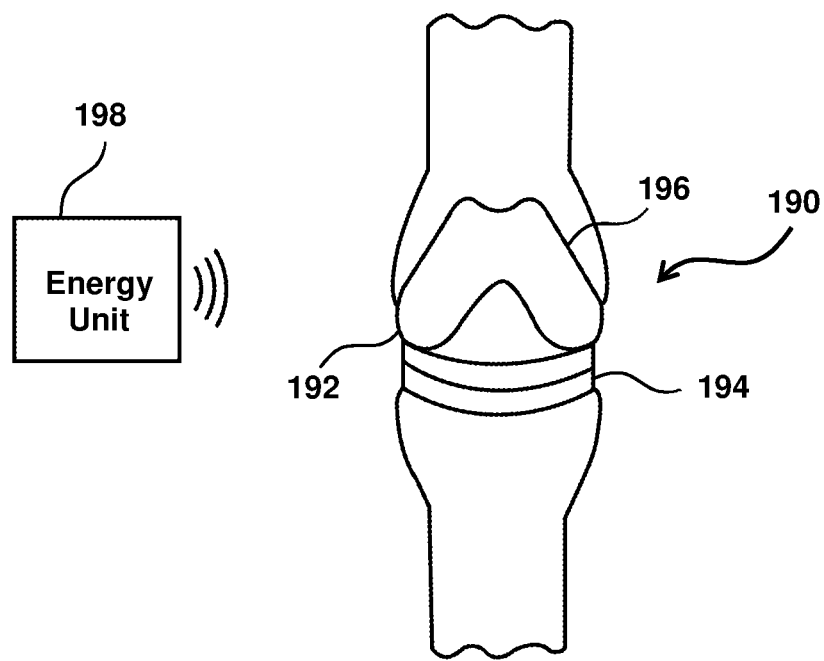
FIG. 23 depicts an exemplary medical implant including an energy sink.

A gender-specific design may also involve altering or controlling the treated area differently for men than for women. Referring to FIG. 23 a medical implant in the form of a prosthetic knee joint 190, including a femoral and tibial component 192 and 194, is provided. The femoral component 192 is configured to provide a localized environmental change in a body of a patient. A localized increase in temperature can have beneficial effects, which include (but are not limited to): aiding in the alleviation of localized pain, fighting of local infections, and increasing vascular flow and permeability of vessels at the treatment site to control delivery of pharmaceutical agent. For example, a localized increasing in temperature increases the permeability of the local tissue, allowing for an increased and more efficient absorption of the pharmaceutical agent into the treatment site.

The femoral component 192 includes an energy sink 196, wherein the energy sink 196 can be used to control the localized temperature of the surrounding tissue. For example, the energy sink 196 can be a heat sink, wherein the heat sink 196 is charged by an internal or external energy unit 198. The heat sink 196 produces a local increase in temperature.

The male and female genders react differently to localized changes in temperatures. For example, a localized increase in temperature of B degrees may have beneficial effect on a female, but no effect on a male. As a result of the differing effects on the male and the female genders, the applied energy is gender dependent. For example, in a female X amount of energy may be required to heat the heat sink 196 to sufficiently raise the localize temperature to have a beneficial effect. In contrast, in a male, Y amount of energy may be required to heat the heat sink 196 to sufficiently raise the localize temperature to have a beneficial effect, wherein Y is greater than X. In accordance with the present invention, the applied energy and heat sink of a femoral component 192 are designed and configured for gender specific use, taking into account the reactive differences between the female and male genders.

Similarly, a localized change in pH can have similar beneficial effects, which include (but are not limited to): aiding in the alleviation of localized pain, fighting of local infections, and increasing vascular flow and permeability of vessels at the treatment site to control delivery of pharmaceutical agent. For example, a localized increase in pH may increase the permeability of the local tissue, thereby allowing for an increased and more efficient absorption of the pharmaceutical agent into the treatment site.

The energy sink 196 in the femoral component 192 can be a pH sink 196. The pH sink 196 can be incorporated into the femoral component 192 or be positioned separate from the femoral component 192. Therefore, the pH sink 196 may be configured to release a chemical to produce either an increase or decrease in the local pH in order to provide a more gender-specific use. An acidic agent would lower the pH and a basic agent would raise the pH. Such agents are well-known to those of ordinary skill.

The male and female genders react differently to localized changes in pH. For example, a localized increase or decrease in the acidity of the surrounding tissue may have a beneficial effect on a female, but no effect on a male. As a result of the different effects on the male and the female genders, the chemical and release rate thereof is dependent on the gender of the patient. As such, in accordance with the present invention, the pH sink 196 is designed and configured for gender specific use, taking into account the reactive differences between the female and male genders.

Additionally, temperature or pH changes may also be used to induce the release of beneficial enzymes, proteins, hormones, etc. from the cells in the treatment site. For example, a localized increase in acidity and/or temperature can be perceived as a physical damage or an infection to the local area. In response, the local cells may release beneficial proteins, enzymes, hormones, etc.

There are several ways to define how a treatment or device may qualify as being gender specific. One way a treatment or device may be considered gender specific is to identify differences in product design or treatment between men and women. Another way to identify whether a device or treatment is gender specific is to determine who the intended patients are. For instance, a product line having two or more models where at least one model is marketed or designed more for men than women and another model is marketed or designed more for women than men would be gender-specific, and therefore within the scope of the invention. If there are measurable differences between the product design or treatment for men versus women, then another way to identify a product or treatment as gender-specific would be by having these differences meet or exceed a threshold amount. For example, in cases where two or more models are offered to account for gender differences at least one of the varying design parameters will differ by about 5 percent or more, and more preferably will differ by about 10 percent or more.

Thus, differences in a range of sizes of a device may in some cases be by 5 percent or more or by 10 percent or more. Likewise, other measurable differences, such as quantity, concentration, or release rates of medications may differ by these numerical amounts. Of course, skilled artisans would readily appreciate that these differences may be applied to any other measurable design parameter of a device or treatment, including duration, amount, thickness, forces applied, diameter, width, height, volume, density, temperature, pH changes, or the like.

Furthermore, while one exemplary embodiment of a medical implant discussed above refers to a prosthetic knee joint, it is contemplated that the medical implant can be any prosthetic implant for use in a body, including, ankle, knee, hip, spine, neck, wrist, elbow or shoulder implants. Furthermore, the medical implant can be, but is not limited to, tissue, scaffold, biological implants, graft, tissue graft, screws, plate, rods, or similar devices.

Pharmaceutical delivery of medication may also be provided in a gender-specific manner. The release and absorption rates of drugs are different for men and women. Oral medication, for instance, may be absorbed differently due to resorption rates in the stomach, intestine, duodenum, abdomen, or the like. Likewise, intravenous medications can react differently for men and women. The present invention contemplates an improved drug delivery that accounts for gender-specific differences. One such example of an improved, gender-specific drug delivery system is in chemotherapy, which is known for being a thermal gradient drug delivery. Since men and women have different temperatures, diurnal changes, and pH, drug-delivery systems would benefit from accounting for one or more of these differences. For example, dosages and the route of administration (e.g. oral release or intravenous) may be varied for men and women. The initial dosage for men may differ from the initial dosage for women, the amount of drugs used in subsequent doses may differ, and the time period between subsequent doses also may differ between men and women. Thus, a medicine given to a man may involve a second dose 8 hours later, while for women the second dose may be 6 hours later, or based on diurnal curves of men and women.

As noted previously, one consequence of accounting for gender-specific difference in medical treatment is that medical treatment may become more complicated or difficult. This additional complexity, however, can be reduced by providing gender-specific indictors on the devices, packaging, or instructions.

The system includes gender specific packaging material which differentiates use for male and female patients. The packaging material can include labeling or color coding to specify gender usage. For medications, the packaging material can include labeling, inserts, or product information which provides dosage information for both male and female patients.

Figure 24:
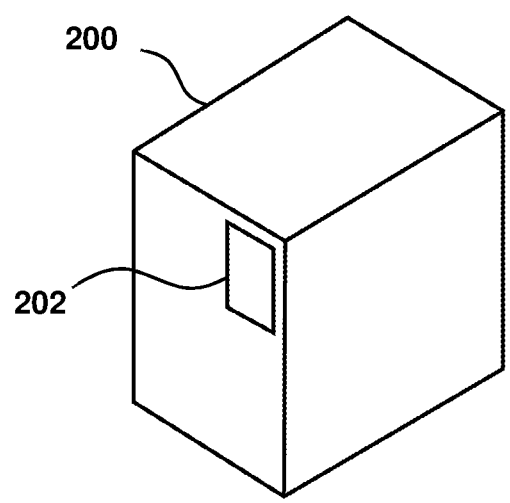
FIG. 24 depicts a representative packaging material of the present invention.
Figure 25:
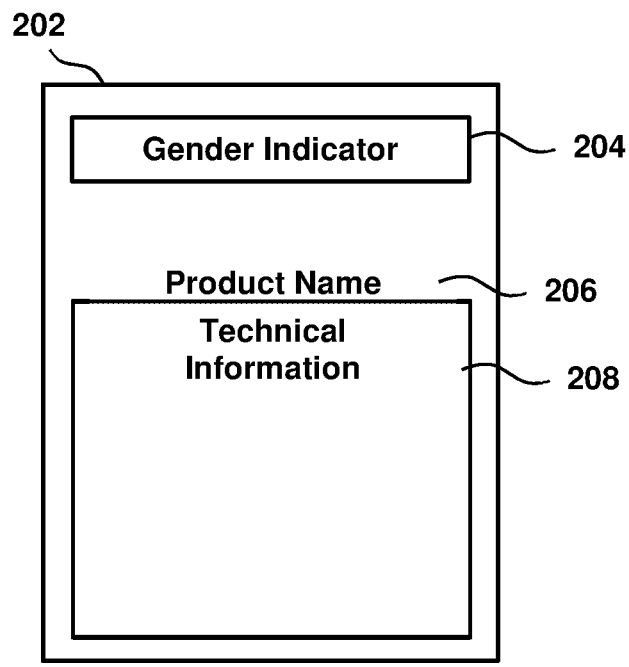
FIG. 25 depicts a representative label affixed to the packaging material of FIG. 24.

Referring now to FIG. 24, a product packaging material 200 of the present invention is shown. The packaging material 200 includes a label 202 affixed thereto or, in the alternative, incorporated into the packaging material 200. The label 202, illustrated in FIG. 25, provides information identifying the contents and usage of the packaging material 200, which can include a gender specifier 204. The gender specifier 204 identifies the gender that the contents of the packaging material 200 are intended for. For example, the gender specifier 204 can be in pictorial, graphic, or text (or combination) form such as "FEMALE" or "MALE." It is contemplated that the text form of the gender specifier 204 can be provided in a variety of languages, depending of the intended country of use.

Alternatively, the gender specifier 204 can be in the form of a color coding, wherein a first color is used to indicate a female gender and a second color is used to indicate a male gender. The first and second colors may be selected from colors that are recognizable as gender indicators. For example, to indicate a female gender the first color can be pink while blue may be used to indicate a male gender. However, it is contemplated that first and second colors can be any colors which are readably discernable as indicators of gender. The color coded gender specifier 204 is depicted as incorporating only a portion of the label 202. However, it is contemplated that the entire label 202 can be color coded to specify gender.

In a further embodiment, the gender specifier 204 can be a symbolic form for representing female and male genders. For example, the gender specifier 204 can be the western culture ideograms for female and male genders, namely "♀" for the female gender and "♂" for the male gender. However, it is contemplated that gender symbols can be any symbols which are readably discernable as indicators of gender.

The label 202 can include additional information, including, the product name 206 and product technical information 208. The product name 206 can be a name used by the company for the product, used to identify the origin of the product, such as CHARITE owned by DePuy Spine, Inc., for an artificial disc. Alternatively, the product name can be a generic or descriptive name of the product, such as ARTIFICIAL DISC. Additional technical information 208 can be provided, such as information relating to the size, material, date of manufacture, lot or control number, etc.

In an alternative embodiment, the packaging material 200 is the gender specifier. For example, the packaging material 200 can be color coded to indicate gender, wherein a first color is used to indicate a female gender and a second color is used to indicate a male gender. The first and second color are selected from colors that are recognizable a gender indicators. For example, to indicate a female gender the first color can be the color pink and to indicate a male gender the second color can be the color blue. However, it is contemplated that first and second colors can be any colors which are readily discernable and indicators of gender.

Figure 26:
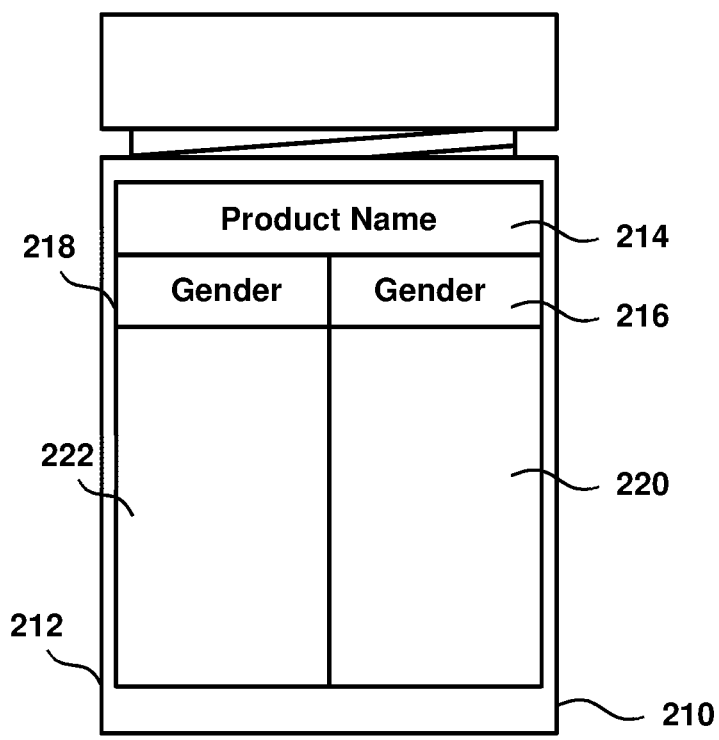
FIG. 26 depicts a representative medicine container of the present invention.

Referring to FIG. 26, an exemplary medicine container 210 is provided, wherein the medicine container 210 includes a label 212 affixed thereto. The label 212 provides information identifying the contents 214 and usage of the enclosed medicine. The usage information includes the recommend dosage for each gender, wherein gender specifiers 216 and 218 annotate the gender dosage information 220 and 222. As described above, the gender specifiers 216 and 218 can be in a text form, such as "FEMALE" and "MALE." Alternatively, the gender specifiers 216 and 218 can be in the form of a color coding or in symbolic representations.

In an alternative embodiment, a product insert can be provided in the medicine container 210. Similar to the label 212, the product insert can provide information identifying the contents and usage of the enclosed medicine, which can include gender specifiers used in conjunction with dosage information.

Another technology that may be utilized to provide a gender-specific indicator is RFID chips. RFID chips may be associated with equipment, instruments, or in sterile packaging so that identification of the intended gender for the devices may be quickly determined. This may be of particular benefit where it is difficult to visually determine the gender-specific design. For example, it may be difficult to visually confirm the intended gender of light sensitive therapeutics, internal components, sealed materials, or implanted devices. Likewise, instrumentation kits may involve several tools or devices that would be time-consuming to confirm are all intended for the same gender. By associating an RFID tag with these devices, however, the gender-specific information can be quickly retrieved. In one embodiment, RFID chips provided in packaged gender-specific drugs are used to determine remaining quantities of medicine.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. A system of gender specific pharmaceuticals comprising:
   (i) a first package comprising a first packaging material comprising:
      a pharmaceutical for use by a male positioned within the first packaging material, the pharmaceutical comprising a central nervous system agent; and
      a male specifier appearing on the first packaging material, and a recommended male dosage appearing on the first packaging material and/or a first insert;
   (ii) a second package comprising a second packaging material comprising:
      a pharmaceutical for use by a female positioned within the second packaging material, the pharmaceutical comprising a central nervous system agent; and
      a female specifier appearing on the second packaging material, and a recommended female dosage appearing on the second packaging material and/or a second insert
   wherein the first and second packaging material differentiates use for male and females.

2. The system of claim 1 wherein the recommended male dosage is different from the recommended female dosage based on differences between males and females in rates of drug absorption and/or metabolism.

3. The system of claim 1 wherein the recommended male dosage is different from the recommended female dosage based on differences between males and females in at least one of temperature, diurnal changes, pH changes, hormonal changes, and susceptibility to diseases or medical conditions.

4. The system of claim 1 wherein the pharmaceutical for use by a male is provided as at least one of a tablet, capsule, powder, and liquid and the pharmaceutical for use by a female is provided as at least one of a tablet, capsule, powder, and liquid.

5. The system of claim 1 wherein the male specifier is in pictorial, graphic, or text form and the female specifier is in pictorial, graphic, or text form.

6. The system of claim 1 wherein the pharmaceutical for use by a male is colored with the same color as the male specifier appearing on the first packaging material and wherein the pharmaceutical for use by a female is colored with the same color as the female specifier appearing on the second packaging material.

7. The system of claim 1 further comprising a first RFID tag associated with the first packaging material and a second RFID tag associated with the second packaging material.

8. The system of claim 1 wherein the first packaging material and/or the first insert provides a recommended time period between the recommended male dosages and the second packaging material and/or the second insert provides a recommended time period between the recommended female dosages.

9. The system of claim 8 wherein the recommended time period between the recommended male dosages is different than the recommended time period between the recommended female dosages.

* * * * *